United States Patent
Tsujino et al.

[11] Patent Number: 6,071,527
[45] Date of Patent: Jun. 6, 2000

[54] DEODORANT MICROPHONE COVER AND METHOD OF PRODUCING THE SAME

[75] Inventors: Rieko Tsujino, Kanagawa-ken; Shinichi Nagata; Fumie Osaki, both of Tokyo, all of Japan

[73] Assignees: Asahi Kogaku Kogyo Kabushiki Kaisha; Crealife Corporation, both of Tokyo, Japan

[21] Appl. No.: 08/834,843

[22] Filed: Apr. 10, 1997

[30] Foreign Application Priority Data

Apr. 10, 1996 [JP] Japan ..................................... 8-088014
Jan. 20, 1997 [JP] Japan ..................................... 9-007431

[51] Int. Cl.$^7$ ....................................................... A61L 9/14
[52] U.S. Cl. ........................ 424/404; 424/76.1; 424/76.2; 424/401; 424/402
[58] Field of Search .................. 424/404, 76.1, 424/76.2, 401, 402

[56] References Cited

U.S. PATENT DOCUMENTS

| | | | |
|---|---|---|---|
| 4,761,366 | 8/1988 | Nakajima et al. | 435/2 |
| 4,800,884 | 1/1989 | Heide et al. | 128/419 R |
| 5,310,548 | 5/1994 | Tsuru et al. | 424/76.3 |
| 5,545,240 | 8/1996 | Tsuru et al. | 55/479 |
| 5,567,231 | 10/1996 | Yokoo et al. | 96/153 |

FOREIGN PATENT DOCUMENTS

| | | |
|---|---|---|
| 57-12409 | 3/1982 | Japan . |
| 60-35016 | 2/1985 | Japan . |
| 61-47401 | 3/1986 | Japan . |
| 62-227932 | 10/1987 | Japan . |
| 63-44997 | 2/1988 | Japan . |
| 1-47581 | 10/1989 | Japan . |
| 63-267421 | 11/1998 | Japan . |
| 685457 | 9/1967 | South Africa . |
| 9003219 | 4/1990 | WIPO . |

OTHER PUBLICATIONS

Derwent Abstract No. 88–094874.
Derwent Abstract No. 87–318665.
Derwent Abstract No. 85–084087.
An English Language Abstract of JP 61–47401.

*Primary Examiner*—Jose' G. Dees
*Assistant Examiner*—Kathryne E. Shelborne
*Attorney, Agent, or Firm*—Greenblum & Bernstein, P.L.C.

[57] ABSTRACT

An antibacterial deodorant cover for a microphone which includes a matrix member, such as an organic polymeric substance, and having a predetermined configuration. The matrix member carries a calcium phosphate compound having a Ca/P ratio in the range of about 1.0 to 2.0. The antibacterial deodorant cover further includes a device for fixing the matrix member to a head of the microphone.

51 Claims, 26 Drawing Sheets

DEODORANT MICROPHONE COVER AND METHOD OF PRODUCING THE SAME

BACKGROUND OF THE INVENTION

1. Field of the Invention

The present invention relates to an antibacterial deodorant cover for covering the head of a microphone, and a method of producing such a cover.

2. Description of the Related Art

Recently, "karaoke" (vocal-free music) has been widely enjoyed all over the world. In karaoke, people sing songs using one or more microphones.

In karaoke booths, bars and other such places, the same microphone is repeatedly used by a large number of different singers. Accordingly, the microphone becomes very unclean and unsanitary due to undesirable contaminants such as saliva, food residues from the mouth, etc., making contact with the head of the microphone. These contaminants should be completely removed from the microphone each time it is used before it is given to the next singer. However, most of the time the microphone is repeatedly used after merely wiping the head with a cleaning cloth or the like, and neither a specific hygienic treatment nor a cleaning treatment is applied to the microphone.

SUMMARY OF THE INVENTION

One object of the present invention is to provide an improved antibacterial deodorant microphone cover which ensures hygienic maintenance of the head of the microphone for an extended period of time, thus aiding in the prevention of contamination of the head during repeated use thereof. Another object of the present invention is to provide a method of producing such an improved microphone cover.

To achieve the former object mentioned above, according to an aspect of the present invention, there is provided an antibacterial deodorant cover for a microphone. The antibacterial deodorant cover includes a matrix member consisting of an organic polymeric substance and having a predetermined configuration. The matrix member carries a calcium phosphate compound having a Ca/P ratio in the range of about 1.0 to 2.0. The antibacterial deodorant cover further includes a device for fixing the matrix member to the head of the microphone.

To achieve the latter object mentioned above, according to another aspect of the present invention, there is provided a method for producing an antibacterial deodorant cover for a microphone. The method of production includes the following steps: applying particles of a calcium phosphate compound which has a Ca/P ratio in the range of about 1.0 to 2.0 to a matrix member consisting of an organic polymeric substance; processing the matrix member to which the calcium phosphate particles have been applied to have a predetermined configuration; and making a device for gathering up a peripheral part of the matrix member to fix the matrix member having the predetermined configuration to a head of the microphone.

To achieve the latter object mentioned above, according to yet another aspect of the present invention, there is provided a method of producing an antibacterial deodorant cover for a microphone, the method of production including the following steps: applying particles of a calcium phosphate compound which has a Ca/P ratio in the range of about 1.0 to 2.0 to a matrix member; die forging the matrix member to which the calcium phosphate particles have been applied to have a predetermined configuration; and making a retainer provided with an inserting hole into which a grip of the microphone is fitted, a peripheral portion of the forged matrix member being fixed to the retainer after the grip has been fitted into the inserting hole so as to fix the forged matrix member to a head of the microphone.

To achieve the latter object mentioned above, according to yet another aspect of the present invention, there is provided a method of producing an antibacterial deodorant cover for a microphone, the method of production including the following steps: applying particles of a calcium phosphate compound which has a Ca/P ratio in the range of about 1.0 to 2.0 to a matrix member; die forging the matrix member to which the calcium phosphate particles have been applied to have a predetermined configuration; and making a device for fixing the forged matrix member to a head of the microphone, wherein the fixing device includes a first annular member detachably fixed to an approximate top end of a grip of the microphone with the first annular member surrounding the approximate top end, and a second annular member detachably fitted on the first annular member, and wherein a peripheral part of the matrix member is held between the first annular member and the second annular member when the second annular member is fitted on the first annular member.

It has been found that the antibacterial deodorant microphone cover to which the present invention is applied is capable of maintaining the head of the microphone in a highly hygienic state during repeated use over an extended period of time.

The present disclosure relates to subject matter contained in Japanese Patent Applications No. 08-88014 (filed on Apr. 10, 1996) and No. 09-7431 (filed on Jan. 20, 1997) which are expressly incorporated herein by reference in their entireties.

BRIEF DESCRIPTION OF THE DRAWINGS

The present invention will be more clearly understood from the description as set forth below with reference to the accompanying drawings, wherein.

DETAILED DESCRIPTION

Figure 1:
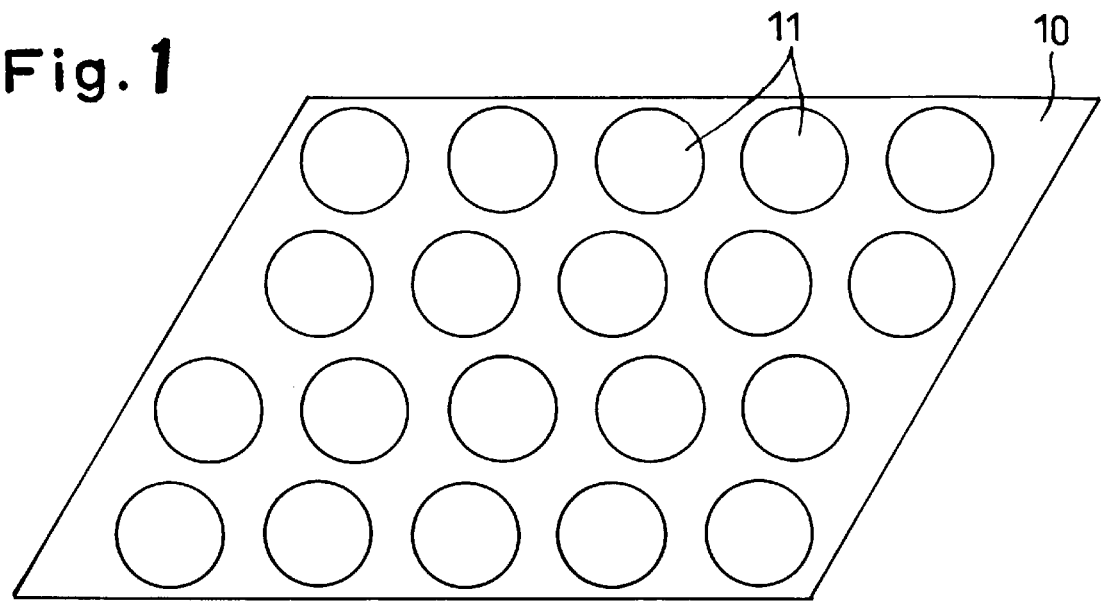
FIG. 1 is a perspective view illustrating the formation of circular matrix members used for producing antibacterial deodorant covers for microphones.

As will be appreciated from the following detailed description, the present invention is based on the high adsorptivity of calcium phosphate compounds. Numerous studies have been made and experiments performed to find the best method for simply and easily applying such adsorptive compounds to a microphone.

An antibacterial deodorant cover used for a microphone to which the present invention is applied is characterized by a matrix member, included with the antibacterial deodorant cover, which preferably comprises an organic polymeric substance and which has a predetermined configuration. The matrix member carries a calcium phosphate compound having a Ca/P ratio in the range of about 1.0 to 2.0. The antibacterial deodorant cover further includes a device for fixing the matrix member to the head of the microphone.

In the practice of the present invention the matrix member may be composed of a non-woven fabric material, a paper material, or a plastic foam (e.g., polyurethane foam) material, etc. For example, a non-woven fabric produced from long filaments of polyethylene terephthalate (PET) disclosed in Japanese Unexamined Patent Publication No. 1-47581 may be used. The PET non-woven fabric is made from long filaments of polyethylene terephthalate having an elongation at breakage of at least 100%, a shrinkage factor in boiling of at least 15% and a circular cross-section having a radius R. Provided that the PET non-woven fabric has an average refraction index, determined at the center of the circular cross-section of the filaments, of $n\|_{(O)}$, another average refraction index, determined at a distance of 0.8R from the center of the circular cross-section of the filaments, of $n\|_{(0.8)}$, and still another average refraction index, determined at a distance of –0.8R from the center of the circular cross-section of the filaments, of $n\|_{(-0.8)}$, with the position of 0.8R apart from the center of the circular cross-section of the filaments being located at a position symmetrical to the position of –0.8R with respect to the center of the circular cross-section of the filaments, the PET non-woven fabric made from long filaments of polyethylene terephthalate would satisfy the following conditions:

$n\|_{(O)} \leq 1.640$, $(n\|_{(0.8)} - n\|_{(O)}) \geq 5.5 \times 10^{-3}$, and $(n\|_{(0.8)} - n\|_{(-0.8)}) \leq 10 \times 10^{-3}$.

In the process of applying the above-mentioned calcium phosphate compound to the matrix member, when the matrix member comprises paper, non-woven fabric or the like, the calcium phosphate compound can be applied to the matrix member when the paper, non-woven fabric or the like is produced. For example, when paper is used as the matrix member, in the process of making the paper, the calcium phosphate particles may be dispersed in the pulp slurry.

Similarly, when the non-woven fabric is used as the matrix member, in the process of making the non-woven fabric, the calcium phosphate compound may be added. For example, when the non-woven fabric used as the matrix member is made of fibers of thermoplastic polymers such as polyethylene fibers, polyurethane fibers, polyester fibers or other fibers, such fibers may be impregnated or coated with an aqueous dispersion of the calcium phosphate particles, followed by heating the impregnated or coated non-woven fabric at a temperature equal to or higher than a softening point of the non-woven fabric, thereby producing the non-woven fabric having the calcium phosphate particles. If necessary, the aqueous dispersion used herein may contain a binder or binding material, for example, polyacrylic esters such as sodium polyacrylate and isobutyl acrylate. Further, when plastic foam is used as the matrix member, calcium phosphate particles may be applied to the matrix member by dipping the plastic foam in a slurry of the calcium phosphate particles and drying the dipped plastic foam.

In the antibacterial deodorant cover of the present invention, a fixing device is provided in combination with the above-mentioned calcium phosphate-carrying matrix member. The fixing device is used to fix the calcium phosphate-carrying matrix member which has been formed into a desired configuration, to the head of a microphone. The fixing device may be a device for gathering up a peripheral part of the matrix member so that the gathered part tightly engages with the neck of the microphone under the head thereof.

For example, the fixing device may include a band, a part of which can be fixed to the matrix member. The band may be made of a flexible plastic, paper, fabric, rubber or the like. An adhesive is provided on at least one end of the band. In this case, when the matrix member is fixed to the head of the microphone, a peripheral part of the matrix member is first gathered using the band with the matrix member placed on the head of the microphone, and subsequently the end of the band which bears the aforementioned adhesive is attached to an appropriate part of the band so as to close the band.

The fixing device may consist of a loop opening formed in a peripheral portion of the matrix member, and a string positioned in the loop opening for gathering the peripheral portion. The string may be made of fabric, rubber, etc.

The fixing device may be in the form of stretchable pleats formed on a peripheral portion of the matrix member.

Further, in the case where the matrix member is made of non-woven fabric or plastic foam, the matrix member may be die-forged using shaping dies with heat at an appropriate temperature so as to have a predetermined three-dimensional configuration or shape which corresponds to that of the head of the microphone. For this die-forged matrix member, the fixing device may be composed of a loop opening formed in a peripheral portion of the die-forged matrix member, and a ring member, at least a part of which is positioned in the loop opening. The ring member may be a double-winding ring, with a part of the ring (preferably one winding ring part thereof) being positioned in the loop opening so that the remaining part (the other one winding ring part thereof) is positioned out of the loop opening.

The matrix member may be provided thereon with any pattern or patterns, for instance, a picture, a cartoon character, etc. In this case, if a wide variety of covers having different types of patterns are prepared in advance, the user of the microphone can freely select a cover having his or her desired pattern from the wide variety of covers.

The fixing device used in combination with the matrix member may include a retainer prepared separately from the matrix member to be fitted around the grip of the microphone under the head thereof, and a fixing portion formed integrally with a peripheral portion of the matrix member to be fixed to the retainer. Preferably, in this case with the retainer and the fixing portion to be fixed to the retainer, the matrix member is die-forged using shaping dies with heat at an appropriate temperature so as to have a predetermined three-dimensional configuration or shape which corresponds to that of the head of the microphone. In this case, the fixing portion of the matrix member may be fixed to the retainer using any fixing device such as set screws, adhesive, Scotch tape, etc. Preferably, the fixing portion of the matrix member is fixed to the retainer using double-sided adhesive tape (double coated tape) or VELCRO composed of a pair of tapes, i.e., a hook tape and a loop tape. In the case of using double-sided adhesive tape, preferably, one side of the double-sided adhesive tape is previously fixed to that surface of the fixing portion which faces the retainer, and the other side of the double-sided adhesive tape is exposed to be adhered to the retainer when the matrix member is fixed to the head of the microphone. In the case of using VELCRO, preferably, one of the hook tape and the loop tape is fixed to that surface of the fixing portion which faces the retainer, and the other hook tape or loop tape is fixed to that surface of the retainer which faces the fixing portion, so that the fixing portion is fixed to the retainer through the hook tape and the loop tape. In either case of using double-sided adhesive tape or VELCRO, the used antibacterial deodorant cover can be easily replaced with a new one.

Instead of using double-sided adhesive tape, VELCRO or the like, an annular fixing member which fits on the retainer with the fixing portion of the matrix member held between the annular fixing member and the retainer can be used. Preferably, the annular fixing member includes a cushioning medium at least along a peripheral edge of the annular fixing member. The cushioning medium is preferably made of rubber or polyurethane foam.

The retainer is preferably formed to have a radial length sufficient to keep the head of the microphone off a horizontal plane (e.g., an upper surface of a table) when the microphone is placed on the horizontal plane, under the condition that the retainer is properly fitted on the grip of the microphone under the head thereof. With this structure, the retainer also functions as a mike stand. The retainer is preferably made of a cushioning material such as rubber, polyurethane foam, any plastic or elastic material of synthetic resin, paperboard, wood, etc. It is preferred that at least a peripheral edge of the retainer be made of a cushioning medium.

Preferably, the retainer is formed so as to be capable of fitting on the grip of the microphone under the head thereof through the retainer's own elasticity. However, the retainer may be fixed to the grip of the microphone under the head thereof by using any fixing device such as adhesive, adhesive tape, a set screw, or the like.

In the practice of the present invention, the calcium phosphate compound to be applied to the matrix member is preferably in the form of particles having a Ca/P ratio in the range of about 1.0 to 2.0 and an average particle diameter in the range of about 0.1 to 100 microns. The calcium phosphate compound is a substance having an excellent adsorptivity to any odor component in a gas, a variety of substances in a liquid and animal or vegetable cells, and accordingly it can exhibit both a good deodorant effect and a good antibacterial effect.

Typical examples of the calcium phosphate compound, although they are not restricted to the below-mentioned, include different types of apatites such as hydroxyapatite, fluorapatite and the like, tribasic calcium phosphate, tetrabasic calcium phosphate, monobasic calcium phosphate and others. These calcium phosphate compounds may be prepared using any conventional production method well-known in the art, and also they may be used alone or as a mixture of two or more compounds.

In addition to the calcium phosphate compound, the matrix member may additionally contain any adsorptive agent such as titanium dioxide, activated carbon, zeolite, molecular sieve and others.

Further, a liquefied calcium phosphate compound may be used as the calcium phosphate compound. The liquefied calcium phosphate compound is a liquid obtained upon the fermentation and aging of a fractured mixture composed of about 1 to 80 parts by weight, in total, of the calcium phosphate compound having a Ca/P ratio in the range of about 1.0 to 2.0 and eggshell powder, and about 10 to 50 parts by weight of starch and/or grain powder.

The calcium phosphate compound used may be in the form of powder, particles or granules, or porous particles or granules. However, the calcium phosphate compound should have an average particle diameter in the range of about 0.1 to 100 microns. The calcium phosphate particles having a particle diameter of less than about 0.1 microns are liable to be aggregated, thereby causing difficulty in uniformly dispersing the particles in water. On the other hand, the calcium phosphate particles having a particle diameter above about 100 microns exhibit a reduction in adsorptivity and other functions, in addition to the deterioration of touch of the produced matrix member. In addition, it is preferred that the calcium phosphate particles have a specific surface area of at least about 0.1 $m^2/g$. A specific surface area of less than about 0.1 $m^2/g$ will exhibit unsatisfactory functions such as adsorptivity.

The powder or particles of the calcium phosphate compound satisfying the above-mentioned particle diameter requirements can be produced using any well-known method. For reference, the production of the porous granules of the calcium phosphate compound will be described hereafter.

The porous calcium phosphate granules can be produced from starting particles which are crystalline particles of the calcium phosphate compound synthesized in a well-known wet process. To a slurry of the starting particles is added an additive such as a viscosity modifier, particles of an organic compound capable of being dissipated upon heating, or fibers. The slurry as a suspension, such as an aqueous slurry, is then directly spray-dried or subjected to other treatments to form secondary particles, or is spray-dried or treated according to other methods to form secondary particles.

The resulting secondary particles are porous particles by themselves, and accordingly they may be used as a starting material without further treatment. If it is desired to obtain porous particles or granules of the calcium phosphate compound having a highly increased porosity, such porous granules can be produced by the following method. Namely, the secondary particles are again suspended in a medium, such as water, to prepare a suspended slurry of the secondary particles, followed by molding the slurry in a wet process or in a dry process under pressure to produce a block body of the calcium phosphate compound. In the preparation of the slurry, any organic compound which may be dissipated from the block body during a subsequent calcination process such as methylcellulose may be added to the slurry in order to assist the formation of pores or cells in the resulting granules. However, such addition of the organic compound may be omitted, because in the absence of such organic compound, a pore size or diameter of the resulting porous granules can be controlled by changing the calcination temperature and other conditions.

The obtained block body is then calcined at a temperature ranging from about 500° C. to about 1300° C. A calcination temperature of less than about 500° C. is insufficient to complete thermal dissipation of the organic compound and calcination of the block body. Additionally, if the calcination of the block body is carried out at an elevated temperature of more than about 1300° C., an excessively densified calcined body may be produced or an undesired decomposition of the calcium phosphate may occur. The thus calcined block body is pulverized and then classified or sieved to obtain porous granules having the desired particle diameter. The pore size of the resulting porous granules can be controlled by suitably varying the size of the crystalline particles of the calcium phosphate compound in the starting slurry used in the preparation of the secondary particles, the viscosity of the slurry, additives and others.

In the antibacterial deodorant cover of the present invention, the rate (carrying rate) of the calcium phosphate compound content of the polymeric matrix member can be widely varied depending upon various factors such as the particle diameter of the calcium phosphate compound used. Generally, it is preferred that the rate of the calcium phosphate compound content of the polymeric matrix member be about 1 to 65% by weight, and more preferably, in the range of about 5 to 40% by weight. When the rate is less than about 1% by weight, only slight effects will be produced by the use of the calcium phosphate compound. When the rate is more than about 65% by weight, only a slight increase in effects will result from the addition of the calcium phosphate compound.

A method of producing the antibacterial deodorant microphone cover to which the present invention is applied is characterized by the following steps of: applying particles of a calcium phosphate compound which has a Ca/P ratio in the range of about 1.0 to 2.0 to a matrix member such as composed of an organic polymeric substance; processing the matrix member to which the calcium phosphate particles have been applied to have a predetermined configuration; and making a device for gathering up a peripheral part of the matrix member to fix the matrix member having the predetermined configuration to the head of the microphone. Namely, after the matrix member carrying the calcium phosphate particles has been prepared, a piece having the desired configuration is cut out of the matrix member carrying the calcium phosphate particles, and then the cut piece is fixed to the head of the microphone by gathering up a peripheral part of the cut piece through the gathering device.

In addition to the above production method, another method of producing an antibacterial deodorant cover for a microphone to which the present invention is applied is characterized by the following steps of: applying particles of a calcium phosphate compound which has a Ca/P ratio in the range of about 1.0 to 2.0 to a matrix member; die-forging the matrix member to which the calcium phosphate particles have been applied to have a predetermined configuration; and making a retainer provided with an inserting hole into which a grip of the microphone is fitted, a peripheral portion of the forged matrix member being fixed to the retainer after the grip has been fitted into the inserting hole so as to fix the forged matrix member to a head of the microphone.

Furthermore, another method of the present invention for producing an antibacterial deodorant cover for a microphone is characterized by the following steps of: applying particles of a calcium phosphate compound which has a Ca/P ratio in the range of about 1.0 to 2.0 to a matrix member; die-forging the matrix member to which the calcium phosphate particles have been applied to have a predetermined configuration; and making a device for fixing the forged matrix member to a head of the microphone, wherein the fixing device includes a first annular member detachably fixed to an approximate top end of a grip of the microphone with the first annular member surrounding the approximate top end, and a second annular member detachably fitted on the first annular member, and wherein a peripheral part of the matrix member is held between the first annular member and the second annular member when the second annular member is fitted on the first annular member.

EXAMPLES

The present invention will be further described with reference to the accompanying drawings, with regard to some working examples thereof. Note, however, that the present invention should not be restricted to these examples.

An aqueous dispersion which contains 10% by weight of porous hydroxyapatite granules having an average granule diameter of 3.5 microns, a specific surface area of 64 $m^2/g$ and a Ca/P ratio of 1.67, and 0.05% by weight of sodium dodecysulfate was prepared. A non-woven fabric serving as a matrix member consisting of 50% by weight of polyethylene and 50% by weight of polyester and having a thickness of 0.2 mm and a weight of 21 $g/m^2$ was impregnated with the aqueous dispersion of the hydroxyapatite granules, and then dried with hot air at 130° C. In the thus obtained hydroxyapatite-carrying non-woven fabric, the rate (carrying rate) of the hydroxyapatite content thereof was determined to be 22% by weight. It should be understood that the hydroxyapatite was almost uniformly applied to the non-woven fabric. It has been also confirmed that the non-woven fabric has a good permeability to air.

FIG. 1 shows the non-woven fabric 10 obtained in the aforementioned manner. After the non-woven fabric 10 is obtained, small pieces of non-woven fabric 11 each having a desired configuration are cut out of the non-woven fabric 10. A circular non-woven fabric piece 11 cut out of the non-woven fabric 10 is used in each of the following first through fourth embodiments of the antibacterial deodorant microphone cover to which the present invention is applied.

Figure 2:
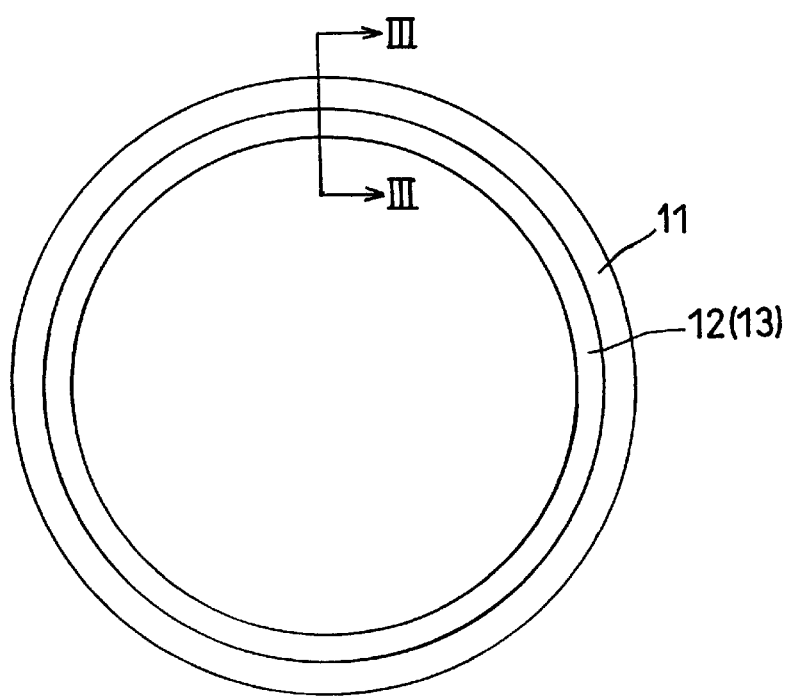
FIG. 2 is a plan view of an antibacterial deodorant microphone cover produced by providing the circular matrix member shown in FIG. 1 with a fixing device.
Figure 3:
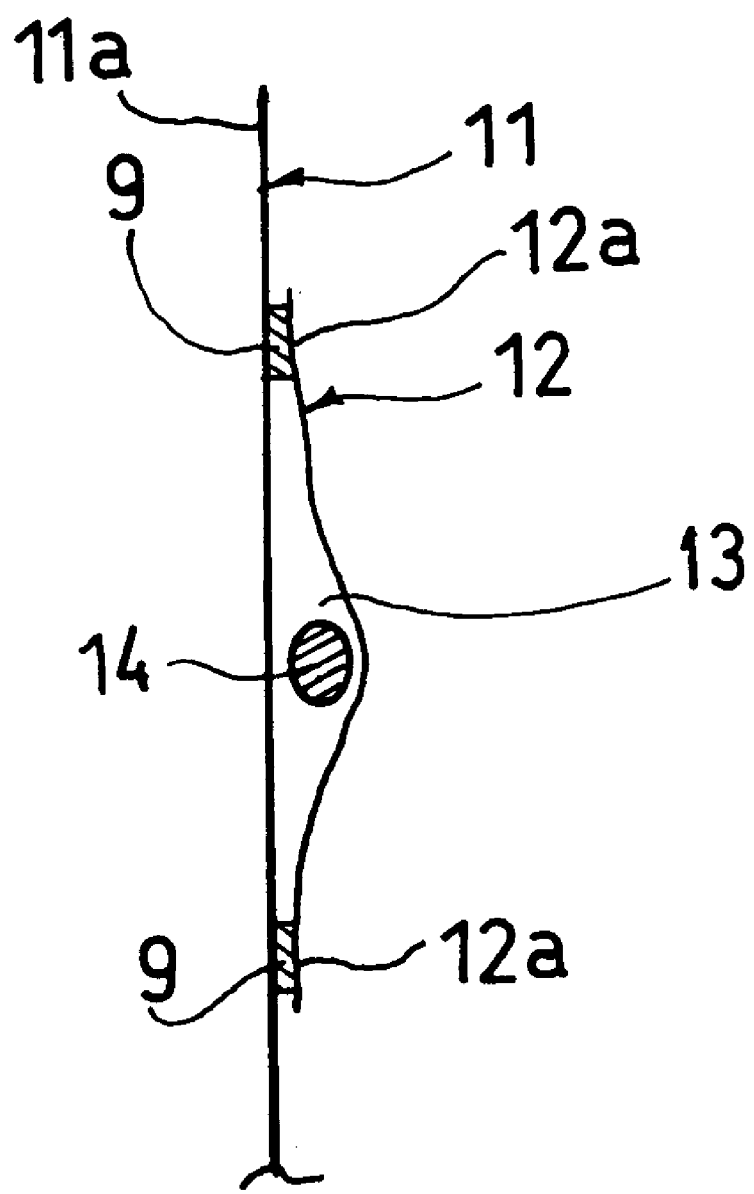
FIG. 3 is a cross-sectional view of the antibacterial deodorant microphone cover taken along line III—III of FIG. 2.
Figure 4:
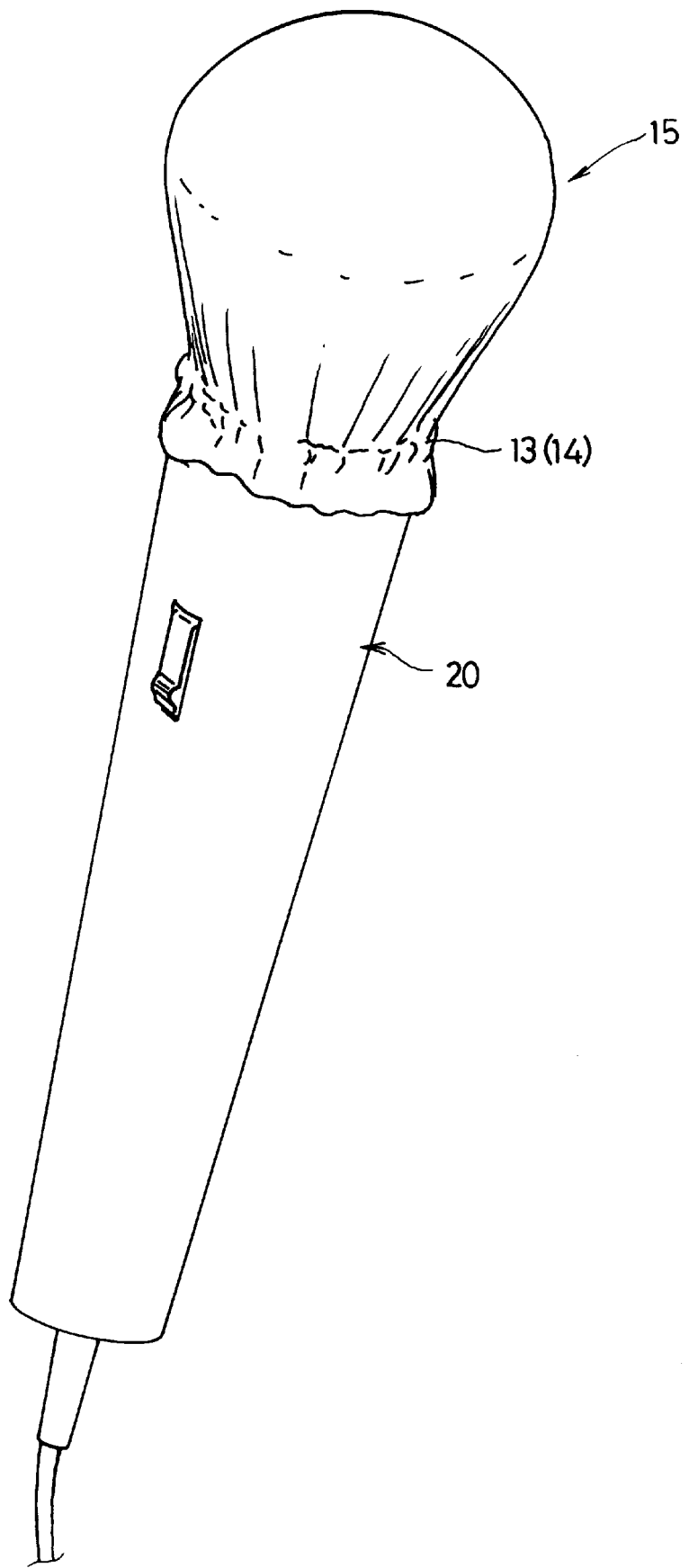
FIG. 4 is a perspective view of a microphone, the head of which is covered by the antibacterial deodorant microphone cover shown in FIGS. 2 and 3.

FIGS. 2, 3 and 4 show the first embodiment of the present invention of an antibacterial deodorant microphone cover. As illustrated in FIGS. 2 and 3, the non-woven fabric piece 11 is provided with a loop opening 13 which is formed by bonding both longitudinal side ends 12a of a ring-shaped fabric 12 to the non-woven fabric 11 by using an adhesive 9. The ring-shaped fabric 12 is fixed to the non-woven fabric piece 11 along a rim 11a thereof. The non-woven fabric piece 11 is further provided with a piece of string 14 made of a fabric whose major part is placed inside the loop opening 13 with both ends of the piece of string 14 being positioned outside the loop opening 13 through a gap (not shown) formed on the fabric 12. The non-woven fabric piece 11 thus obtained having the piece of string 14 along a peripheral part of the non-woven fabric piece 11 is used as an antibacterial deodorant microphone cover 15 as shown in FIG. 4. In other words, after the head of microphone 20 has been covered by the obtained non-woven fabric piece 11, both ends of the piece of string 14 are tied to gather up the peripheral part of the obtained non-woven fabric piece 11 to thereby fix the peripheral part to the neck of the microphone 20 under the head thereof. This completes the antibacterial deodorant microphone cover to cover up the head of the microphone 20.

The antibacterial deodorant microphone cover 15 can be detached from the head of the microphone 20 simply by untying the tied ends of the piece of string 14. Accordingly, the antibacterial deodorant microphone cover 15 can be easily replaced with a new one. In the state shown in FIG. 4 where the antibacterial deodorant microphone cover 15 is fixed to the head of the microphone 20, the antibacterial deodorant microphone cover 15 exhibits both a deodorant effect and an antibacterial effect. In this first embodiment, instead of using the piece of string 14 made of fabric, a rubber ring or band may be positioned in the loop opening 13. With this structure, the microphone cover 15 is put on or taken off the head of the microphone 20 by stretching and expanding the peripheral portion of the microphone cover 15.

Figure 5:
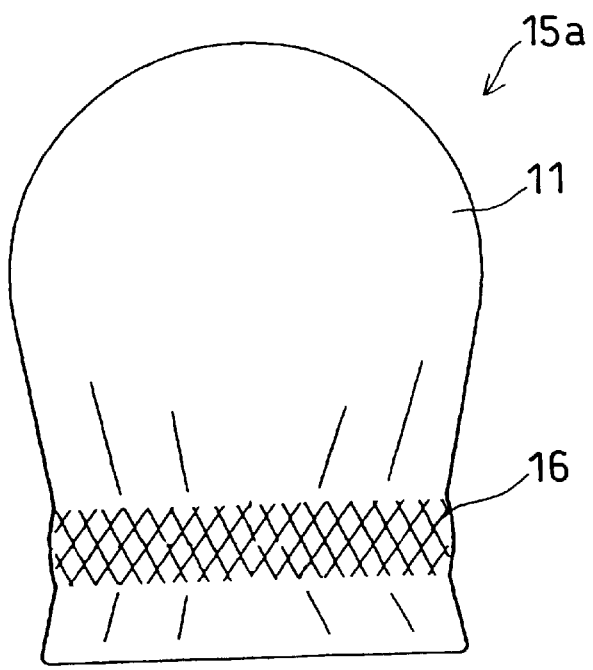
FIG. 5 is a front view of another embodiment of the antibacterial deodorant microphone cover.

FIG. 5 shows the second embodiment of the present invention of the antibacterial deodorant microphone cover. In this embodiment, as shown in FIG. 5, the non-woven fabric piece 11 is provided along a rim thereof with stretchable pleats 16, which complete an antibacterial deodorant microphone cover 15a to cover up the head of the microphone 20.

Figure 6:
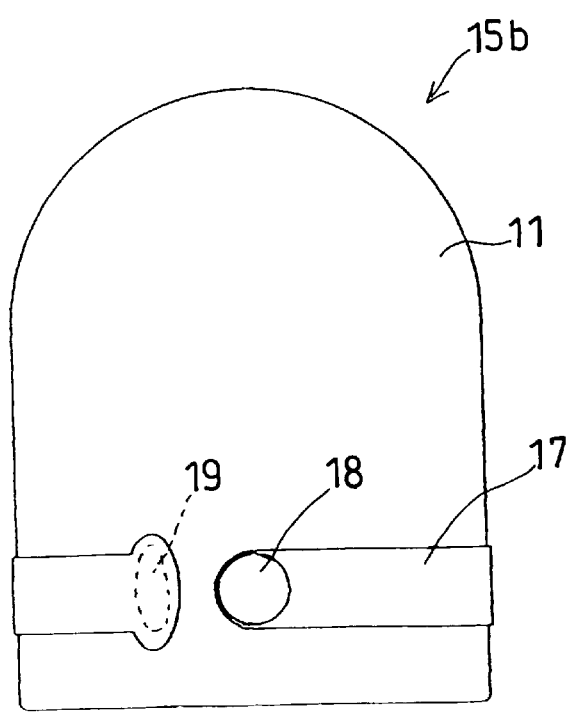
FIG. 6 is a front view of yet another embodiment of the antibacterial deodorant microphone cover.
Figure 7:
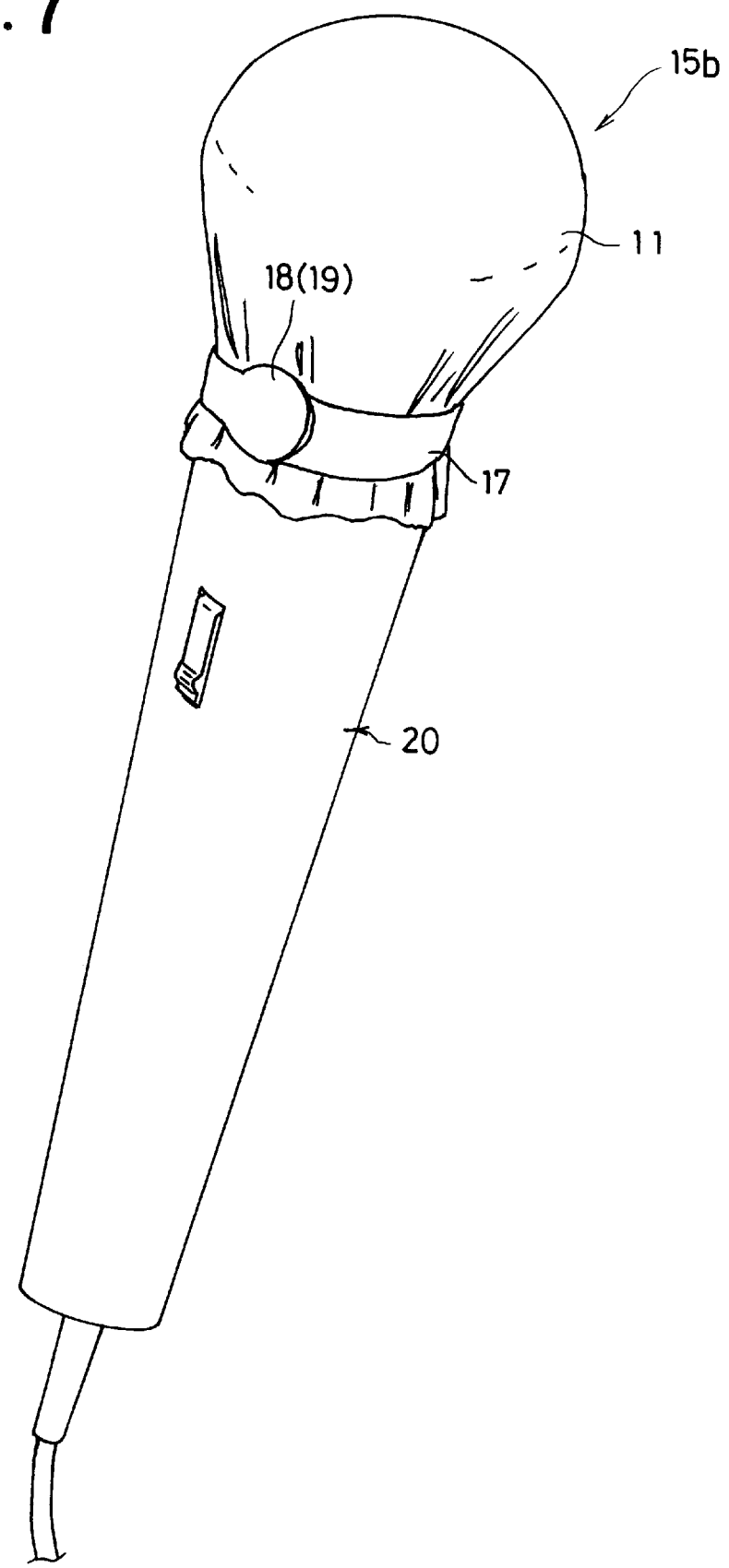
FIG. 7 is a perspective view of a microphone, the head of which is covered by the antibacterial deodorant microphone cover shown in FIG. 6.

FIGS. 6 and 7 show the third embodiment of the present invention of the antibacterial deodorant microphone cover. In this embodiment, instead of using a piece of string or stretchable pleats like the first or second embodiment, a band 17 made of a flexible plastic is used. The band 17 is long enough to surround the neck of the microphone 20 with a peripheral part of the non-woven fabric piece 11 being held between the band 17 and the neck of the microphone 20. A middle portion of the band 17 is fixed to the non-woven fabric piece 11, and double-sided adhesive tape 18 and 19 is provided on both ends of the band. After the non-woven fabric piece 11 having the band 11 is put on the head of the microphone 20, the peripheral part of the non-woven fabric piece 11 is gathered up by the band 17 and subsequently the adhesive tapes 18 and 19 are attached to each other to thereby fix the peripheral part of the non-woven fabric piece 11 to the neck of the microphone 20 under the head thereof, which completes an antibacterial deodorant microphone cover 15b to cover up the head of the microphone 20. Either one of the adhesive tapes 18 or 19 may be omitted. In this case, either adhesive tape 18 or 19 is attached to the other corresponding end of the band 17 when the head of the microphone 20 is covered by the antibacterial deodorant microphone cover 15b. FIG. 7 shows the microphone 20 having the microphone cover 15b fixed to the head thereof using the band 17. Although the band 17 is made of a flexible plastic in this particular embodiment, the band 17 may be made of paper, fabric, rubber or the like.

Figure 8:
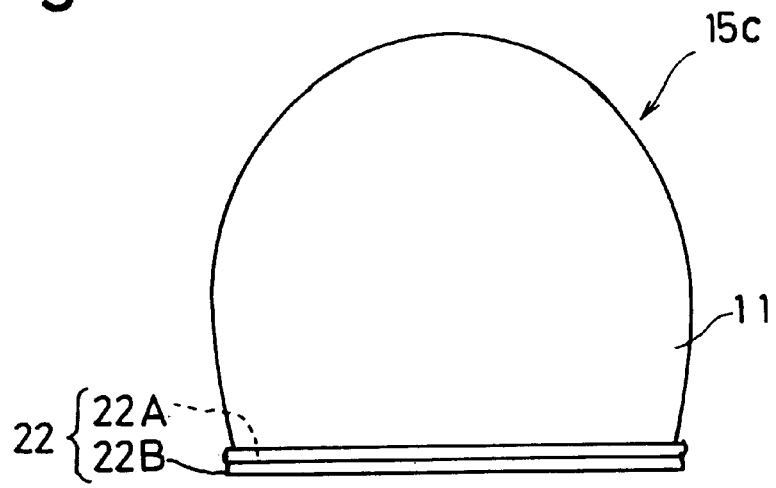
FIG. 8 is a front view of yet another embodiment of the antibacterial deodorant microphone cover.
Figure 9:
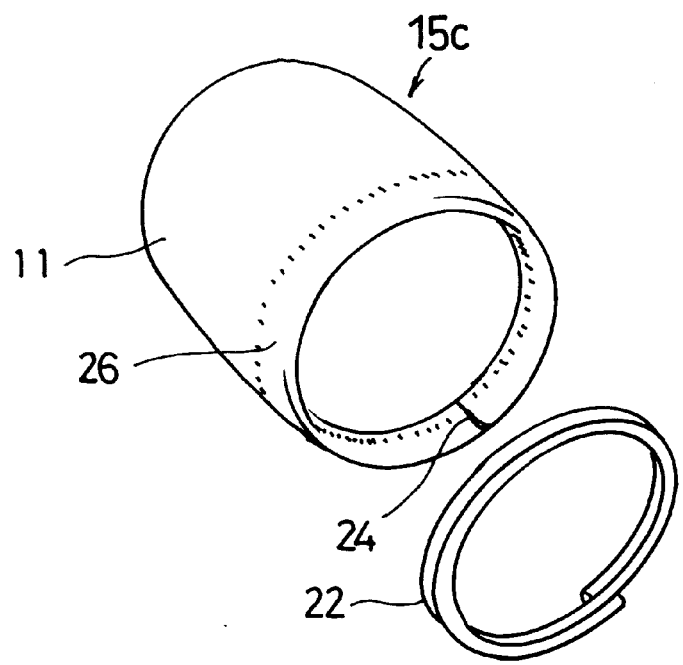
FIG. 9 is a perspective view of the antibacterial deodorant microphone cover shown in FIG. 8 and a double-winding ring which is to be fixed to the antibacterial deodorant microphone cover.
Figure 10:
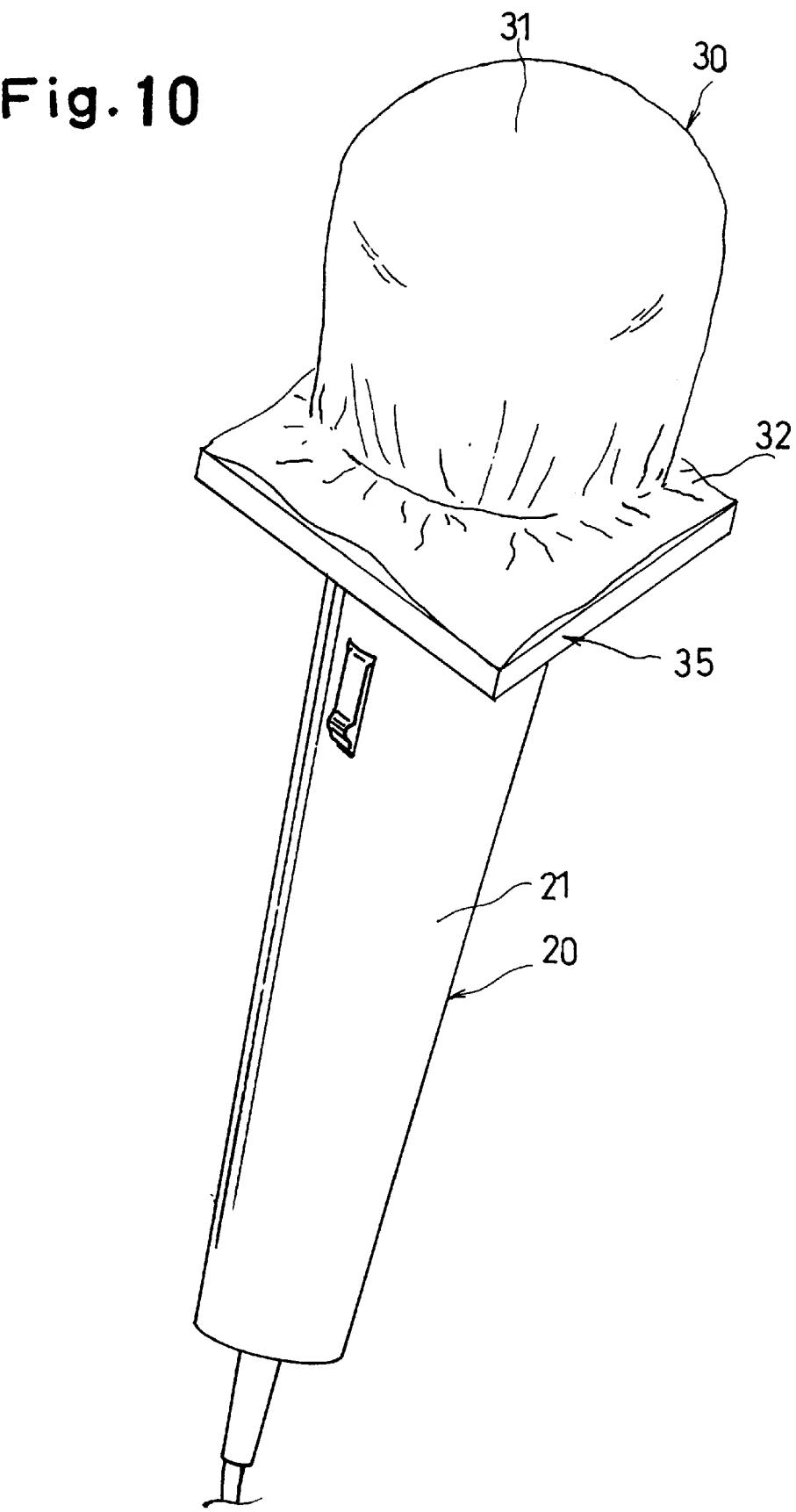
FIG. 10 is a perspective view of a microphone, the head of which is covered by yet another embodiment of the antibacterial deodorant microphone cover.

FIGS. 8 and 9 show the fourth embodiment of the present invention of the antibacterial deodorant microphone cover. In this embodiment, the non-woven fabric piece 11 is die-forged using a pair of shaping dies (not shown) with heat at an appropriate temperature so as to have a predetermined three-dimensional configuration or shape which corresponds to that of the head of the microphone 20. Thereafter, a rim of the forged non-woven fabric piece 11 is inwardly folded up and the endmost part of the rim is melt-welded to the inner surface of the forged non-woven fabric piece 11 to form a loop opening 26. A double-winding ring 22 is half inserted in the loop opening 26 through a gap 24 formed on the folded part of the forged non-woven fabric piece 11, which completes a microphone cover 15c to cover up the head of the microphone 20. As is illustrated in FIG. 8, only half of the double-winding ring 22, i.e., a first ring portion 22A, is inserted into the loop opening 26 so that the first ring portion 22A in the loop opening 26 can fix the microphone cover 15c to the head of the microphone 20 by the biasing force of the double-winding ring 22. The remaining part of the double-winding ring 22, i.e., a second ring portion 22B, which is positioned outside the loop opening 26, directly engages with the neck of the microphone 20 so as to fix the microphone cover 15c to the head of the microphone. Since the second ring portion 22B is exposed to be seen along the rim of the microphone cover 15c, the second ring portion 22B may have aesthetic value. For instance, the second ring portion 22B may be painted in a desired color so as to decorate the microphone 20.

Preferably, the pairs of shaping dies for forging the non-woven fabric piece 11 and the double-winding rings 22 of different sizes are prepared in advance so that they can satisfy the requirements concerning a variety of different head diameters of the microphones used. In the illustrated embodiment, the cover 15c can be easily fitted to the head of the microphone 20 because of the stretchability of the double-winding ring 22. Further, since the non-woven fabric piece 11 is die-forged under heating in conformity with the configuration of the microphone head, few wrinkles are formed along the rim of the microphone cover 15c, thereby improving the exterior appearance of the cover 15c.

In the above-mentioned fourth embodiment illustrated in FIGS. 8 and 9, the double-winding ring 22 is made of a brass-plated steel wire having a diameter of 1 mm. However, it should be noted that the double-winding ring 22 used in the practice of the present invention is not restricted solely to those having the described material, diameter, color, etc. The double-winding ring 22 may be replaced by a different type of ring member, as long as it has a configuration capable of fixing the forged non-woven fabric piece 11 to the head of the microphone 20.

FIGS. 10 to 13 illustrate the fifth embodiment of the present invention of the antibacterial deodorant microphone cover. In this fifth embodiment and the sixth embodiment, which will be discussed later, a non-woven fabric piece is used which is cut out of a processed non-woven fabric produced in a method different from that of producing the non-woven fabric piece 11 used in the above-mentioned first through fourth embodiments. In the fifth or sixth embodiment, similar to each of the above-mentioned first through fourth embodiments, an aqueous dispersion, i.e., an aqueous dispersion which contains 10% by weight of porous hydroxyapatite granules having an average granule diameter of 3.5 microns, a specific surface area of 64 m$^2$/g and a Ca/P ratio of about 1.67, and 0.05% by weight of sodium dodecysulfate, was prepared. After a non-woven fabric composed of long polyester filaments and having a thickness of 0.32 mm and a weight of 150 g/m$^2$ was impregnated with the above aqueous dispersion of the hydroxyapatite granules, the non-woven fabric was dried with hot air at a temperature of 60 to 70° C. In this drying process, since a drying temperature of more than about 80° C. causes thermal shrinkage of the non-woven fabric, the drying temperature was appropriately controlled so as not to exceed 80° C. In the thus obtained hydroxyapatite-carrying non-woven fabric, the rate (carrying rate) of the hydroxyapatite content thereof was determined to be 22% by weight. It should be understood that the hydroxyapatite was almost uniformly applied to the non-woven fabric. It has also been confirmed that the non-woven fabric has a good permeability to air.

The non-woven fabric thus obtained may be cut into small pieces of non-woven fabric each having the desired configuration. The non-woven fabric piece thus obtained is used to make an antibacterial deodorant microphone cover of either the fifth or the sixth embodiment.

In the fifth embodiment, the non-woven fabric piece is die-forged using a pair of shaping dies (not shown) with heat at an appropriate temperature so as to have a predetermined three-dimensional configuration or shape which corresponds to that of the head of the microphone 20 (see FIGS. 10, 11 and 12) to thereby produce an antibacterial deodorant microphone cover 30 to cover up the head of the microphone 20.

The microphone cover 30 is provided with a covering portion 31 with a shape that corresponds to that of the head of the microphone 20 to be capable of covering up the head of the microphone 20. The microphone cover 30 is further provided with a skirt portion 32 (portion to be fixed to the below-described retainer 35) which extends outwardly from the rim of the covering portion 31. The skirt portion 32 is formed to have a configuration corresponding to that of the retainer 35.

Figure 13:
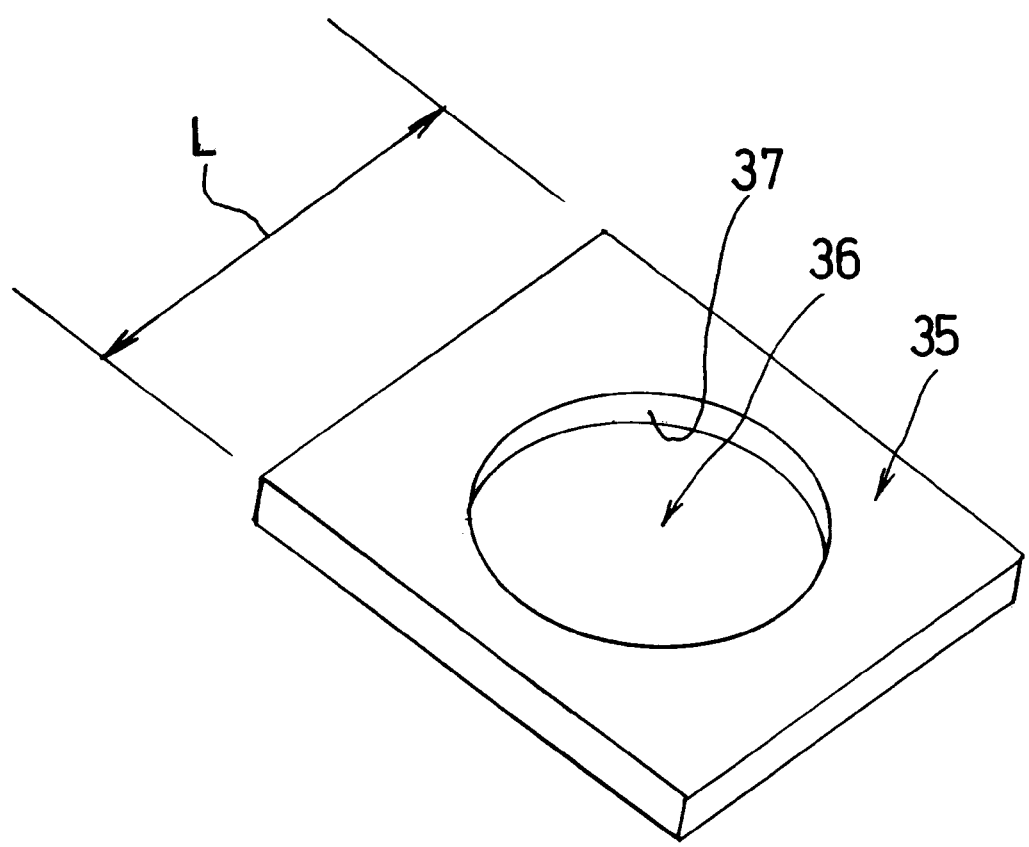
FIG. 13 is a perspective view of the retainer shown in FIG. 11.

FIG. 13 illustrates the retainer 35 which is used when the microphone cover 30 is fixed to the head of the microphone 20. The retainer 35 is made of rubber having moderate elasticity. When viewed from above, the retainer 35 has a substantially square profile. The retainer 35 is provided at its center with a circular hole or opening 36 in which the grip 21 of the microphone 20 is inserted. The diameter of the circular hole is predetermined to be slightly smaller than that of the neck of the grip of the microphone 20 under the head thereof so that the retainer 35 can be fitted on and around the neck of the grip. The retainer 35 is formed such that each side thereof has a length L (see FIG. 13) which is sufficient to keep the head of the microphone 20 off a horizontal plane, e.g., an upper surface of a table, at a predetermined distance when the microphone 20 is placed on the horizontal plane under the condition that the retainer 35 is fitted on the neck of the microphone 20 under the head thereof. Accordingly, the retainer 35 also functions as a mike stand for the microphone 20.

Figure 11:
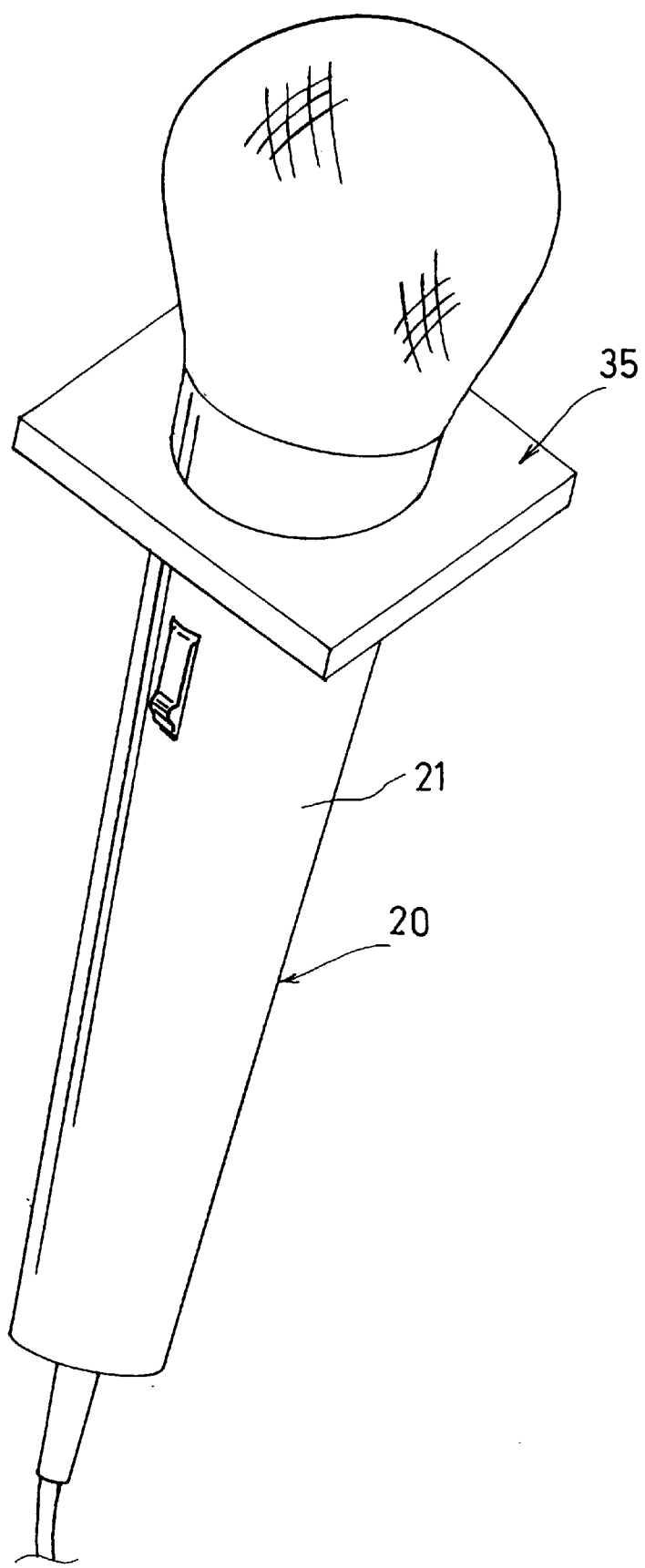
FIG. 11 is a perspective view of the microphone shown in FIG. 10 with a retainer fitted on the grip of the microphone when the antibacterial deodorant microphone cover is removed from the head of the microphone.
Figure 12:
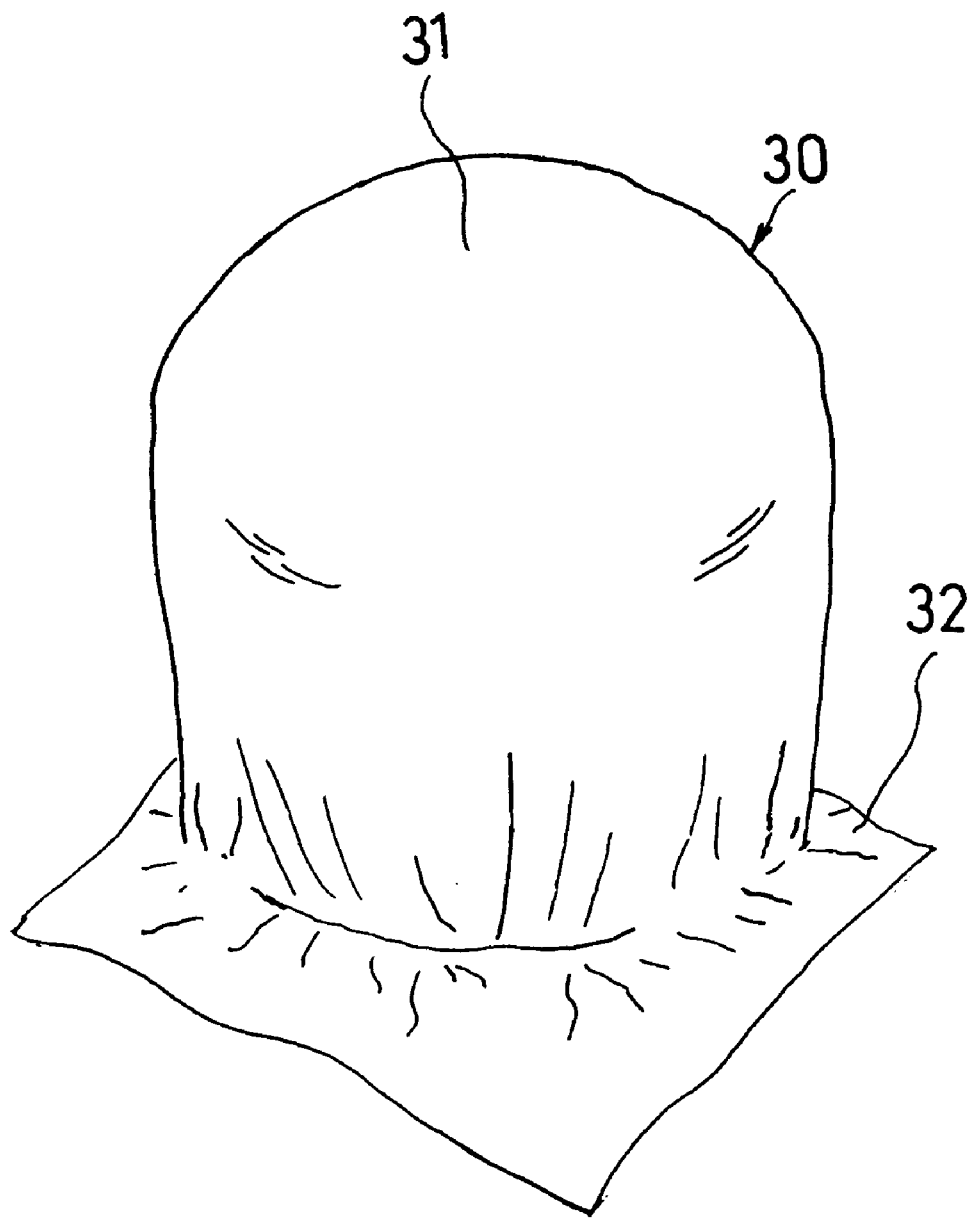
FIG. 12 is a perspective view of the antibacterial deodorant microphone cover shown in FIG. 10.

The retainer 35 is fitted on the microphone 20 by inserting the grip 21 of the microphone 20 into the circular hole 36 from the bottom end of the grip 21. FIG. 11 shows the retainer 35 having been fitted on the neck of the grip 21 of the microphone 20. In FIG. 11, the microphone cover 30 has not yet been fixed to the head of the microphone 20, and therefore, the microphone cover 30 is not shown in FIG. 11.

The grip 21 of the microphone 20 is formed to taper toward the lower end thereof. A circular surface 37 of the microphone-inserting opening 36 of the retainer 35 is also formed to taper to correspond to the tapered grip 21. Due to such a formation, when the retainer 35 is fitted on the grip 21 of the microphone 20, a large contacting area between the circular surface 37 and the corresponding outer peripheral surface of the grip 21, with which the circular surface 37 is in pressing contact, is obtained, thereby the retainer 35 is tightly fitted on the grip 21. In the case where the microphone 20 has a mere cylindrical grip 21, not a tapered grip, the inner peripheral surface 37 should not be formed to taper but formed to be a mere cylindrical surface so as to correspond to the cylindrical grip 21.

After the retainer 35 has been properly fitted on the microphone 20, the microphone cover 30 is put on the head of the microphone 20 with the covering portion 31 fully covering the head of the microphone 20. Thereafter, the skirt portion 32 of the microphone cover 30 is fixed to the retainer 35 using double-sided adhesive tape (not shown). The skirt portion 32 is previously provided on its bottom surface facing the retainer 35 with double-sided adhesive tape such that one side of the double-sided adhesive tape is fixed to the bottom surface of the skirt portion 32 and that a protective seal for covering the other side of the double-sided adhesive tape has not been taken off the other side of the double-sided adhesive tape. The protective seal on the other side of the double-sided adhesive tape is peeled off just before the skirt portion 32 is fixed to the retainer 35. Namely, after the retainer 35 has been fit on the grip 21 of the microphone 20, the protective seal is first peeled off the double-sided adhesive tape provided on the bottom surface of the skirt portion 32, and subsequently the head of the microphone 20 is covered with the covering portion 31 while the skirt portion 32 is fixed to the retainer 35 by fixing the adhesive surface of the double-sided adhesive tape to the retainer 35.

Although double-sided adhesive tape is used as a fixing device for fixing the skirt portion 32 of the microphone cover 30 to the retainer 35 in the aforementioned embodiment, VELCRO composed of a hook tape and a loop tape may be used in place of double-sided adhesive tape.

Using VELCRO, one of the hook tape and the loop tape is fixed to the bottom surface of the skirt portion 32 of the microphone cover 30, while the other of the hook tape and the loop tape is fixed to a corresponding surface of the retainer 35. The hook tape and the loop tape are connected to each other when the microphone cover 30 is fixed to the retainer 35.

In either case, when using double-sided adhesive tape or VELCRO to fix the microphone cover 30 to the retainer 35, the microphone cover 30 can be easily fixed to or removed from the head of the microphone 20. During the time the head of the microphone 20 is covered with the microphone cover 30, the microphone cover 30 exhibits satisfactory deodorizing and antibacterial effects. Note, however, that if desired, instead of using double-sided adhesive tape or VELCRO, any other fixing device such as clips, screws, adhesive or the like may be used to fix the skirt portion 32 to the retainer 35.

Furthermore, another non-woven fabric carrying an increased amount of hydroxyapatite was produced by applying a gravure printing onto the non-woven fabric carrying 22% by weight of hydroxyapatite used in the above-mentioned production of the microphone cover 30. In this production of the non-woven fabric, 30% by weight of porous hydroxyapatite granules having an average granule diameter of 10 microns and a Ca/P ratio of 1.67 were dissolved in an organic solvent such as isopropyl alcohol, to prepare a gravure printing solution. The resulting solution was gravure-printed to the aforementioned non-woven fabric carrying 22% by weight of hydroxyapatite, produced in the above-described production of the microphone cover 30, on a gravure printing plate with a gravure depth of 60 microns. The printed non-woven fabric was then dried with hot air at a temperature 60 to 70° C. In the drying process, since a drying temperature above 80° C. causes shrinkage of the non-woven fabric, the drying temperature was appropriately controlled so as not to exceed 80° C. In the thus obtained hydroxyapatite-carrying non-woven fabric, the rate (carrying rate) of the hydroxyapatite thereof was determined to be 30% by weight. It should be understood that the hydroxyapatite was almost uniformly applied to the non-woven fabric. It has also been confirmed that the non-woven fabric has a good permeability to air. Using the gravure-printed non-woven fabric as the microphone cover, satisfactory results similar to those obtained by using the non-woven fabric carrying 22% by weight of hydroxyapatite and having no gravure printing thereon could be obtained.

Generally, when a microphone is carelessly placed on a table or the like with the switch of the microphone remaining ON, the head of the microphone hits the surface of the table, which generates an undesirable loud and unpleasant noise. However, when the microphone 20 with the microphone cover 30 fitted thereon is used, since the microphone cover 30 has the retainer 35 made of rubber which functions as a cushioning member, the aforementioned loud and undesirable noise is prevented from occurring, or reduced to a negligible amount. This noise is reduced because direct contact between the head of the microphone 20 and the surface of the table or the like is effectively avoided due to the presence of the retainer 35, and shock generated upon placing the microphone 20 on the table or the like can be effectively absorbed by the retainer 35.

The retainer 35 may be made of any other material such as polyurethane foam, plastic, a piece of board paper, a piece of wood or the like. Further, if the retainer 35 has a cushioning material such as rubber at least along a peripheral portion of the retainer 35, the above-mentioned problem concerning a loud and undesirable noise generated upon the head of the microphone making contact with the table, for example, can be effectively avoided.

Figure 14:
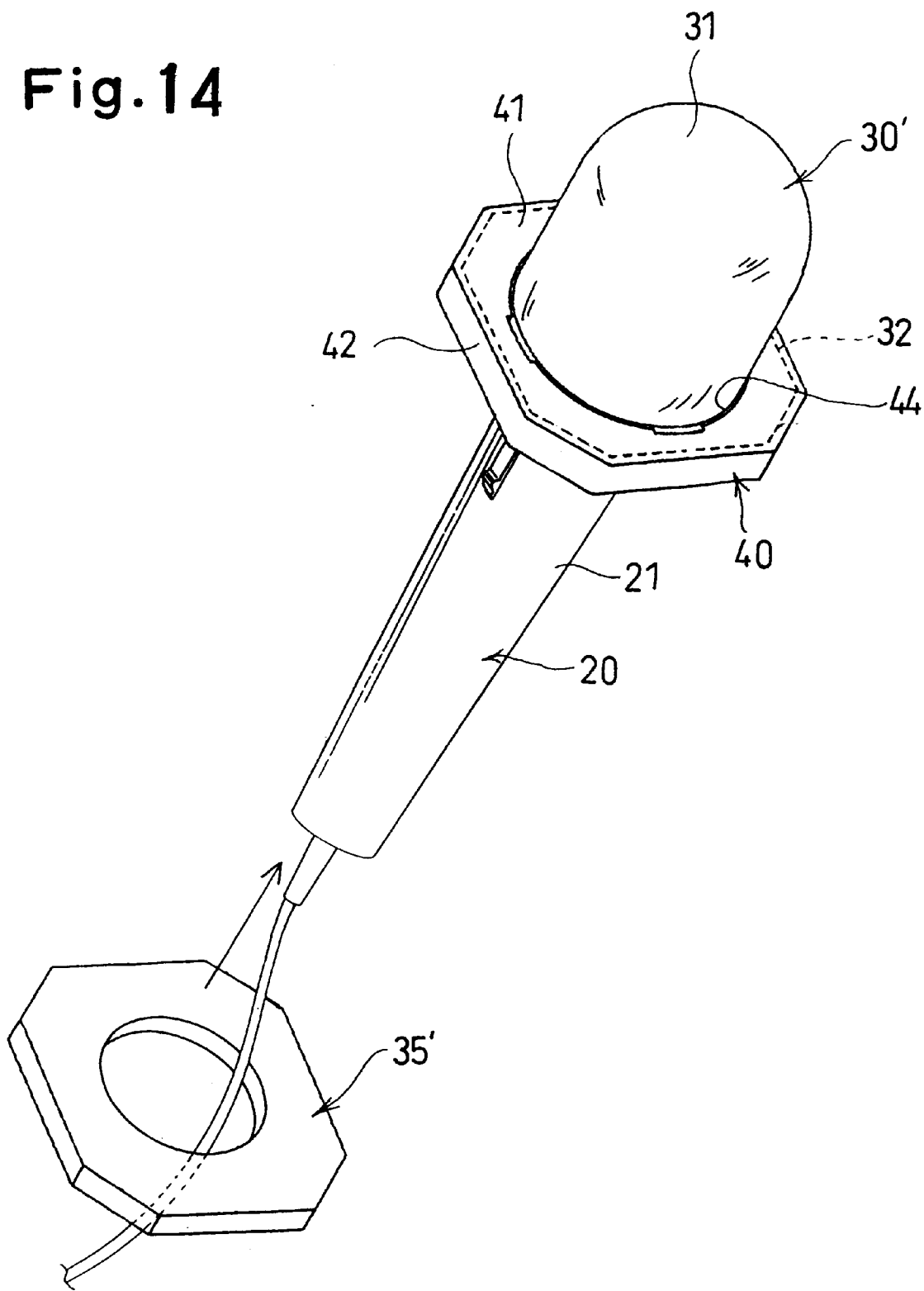
FIG. 14 is a perspective view of a microphone, the head of which is covered by yet another embodiment of the antibacterial deodorant microphone cover.
Figure 15:
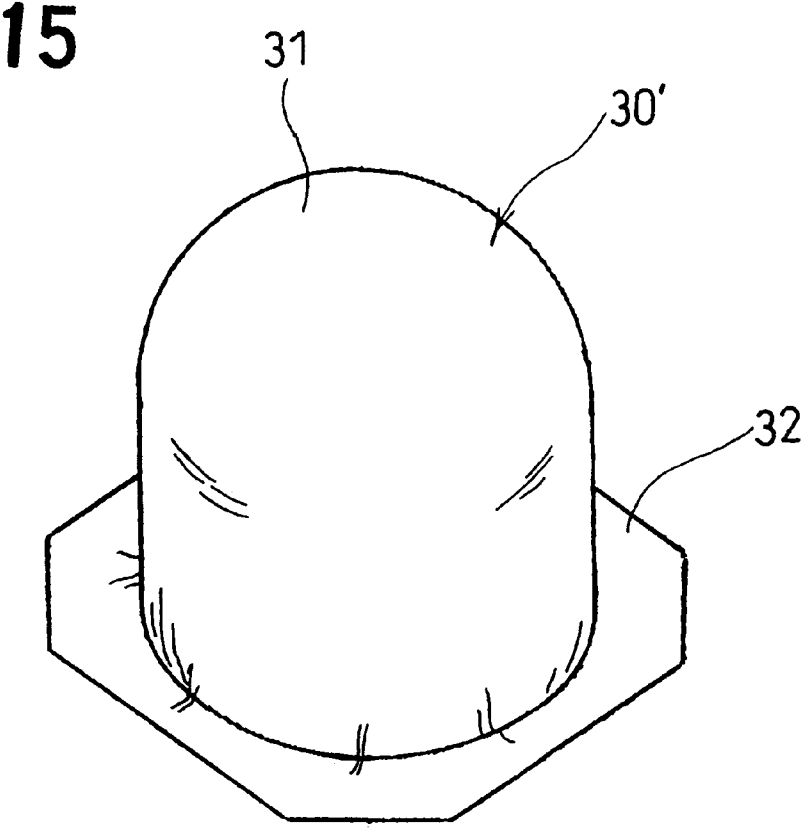
FIG. 15 is a perspective view of the antibacterial deodorant microphone cover shown in FIG. 14.
Figure 16:
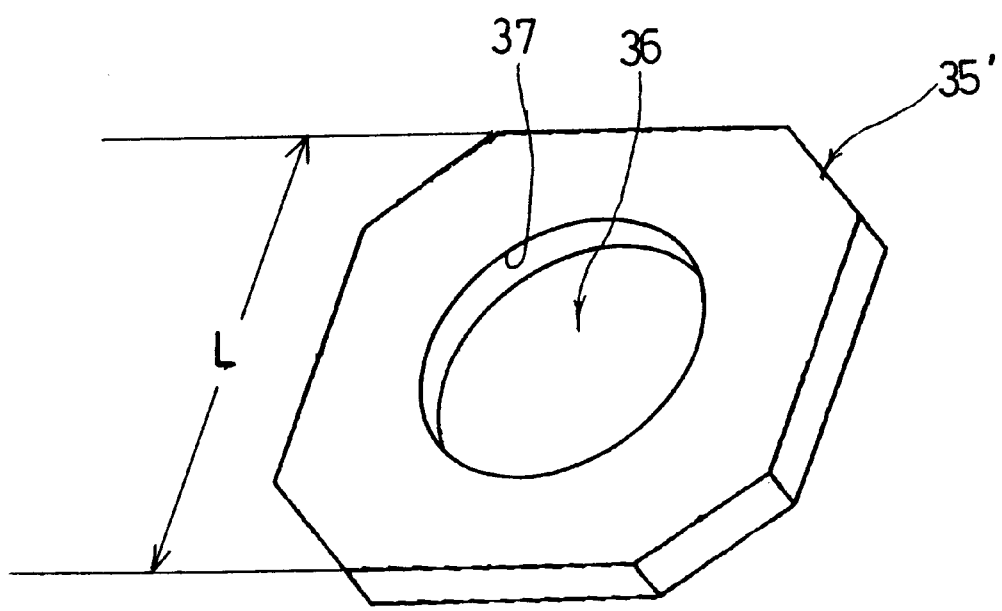
FIG. 16 is a perspective view of the retainer shown in FIG. 14.
Figure 17:
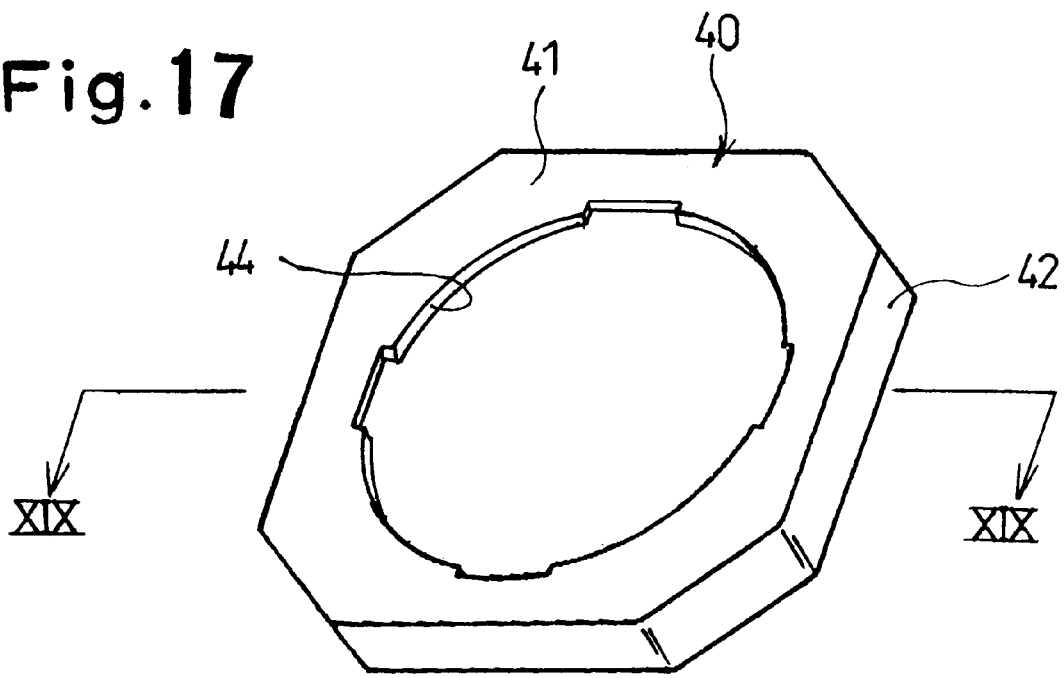
FIG. 17 is a perspective view of the annular mounting member shown in FIG. 14.
Figure 18:
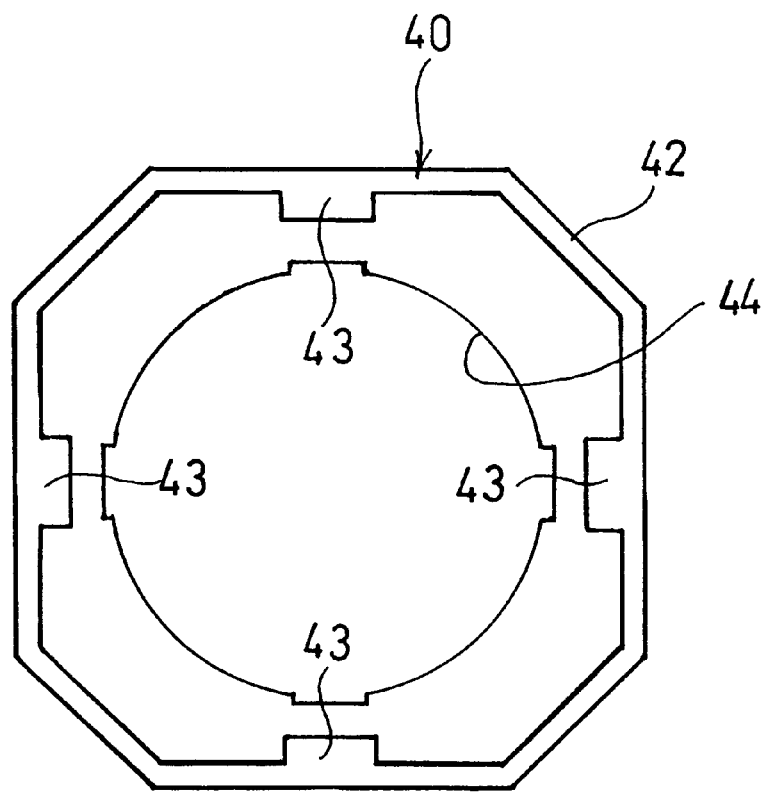
FIG. 18 is a bottom view of the annular mounting member shown in FIG. 17.
Figure 19:
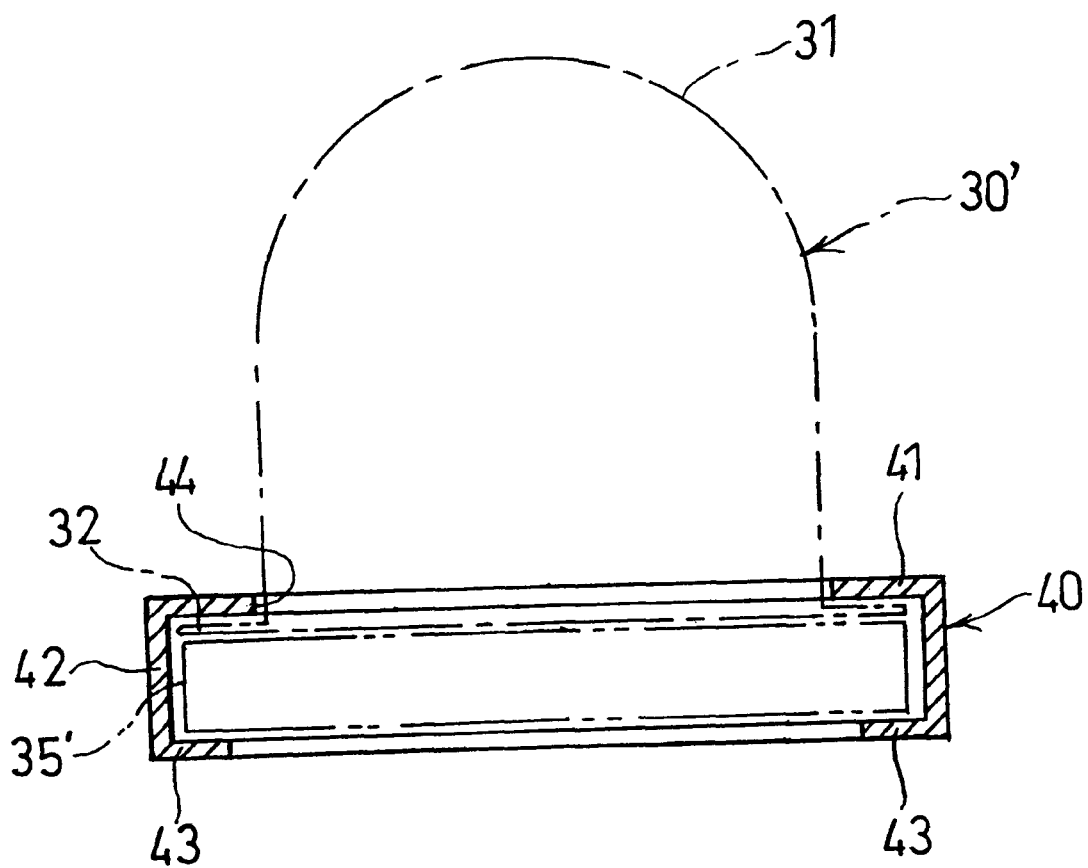
FIG. 19 is a cross-sectional view of the annular mounting member taken along line XIX—XIX of FIG. 17.
Figure 20:
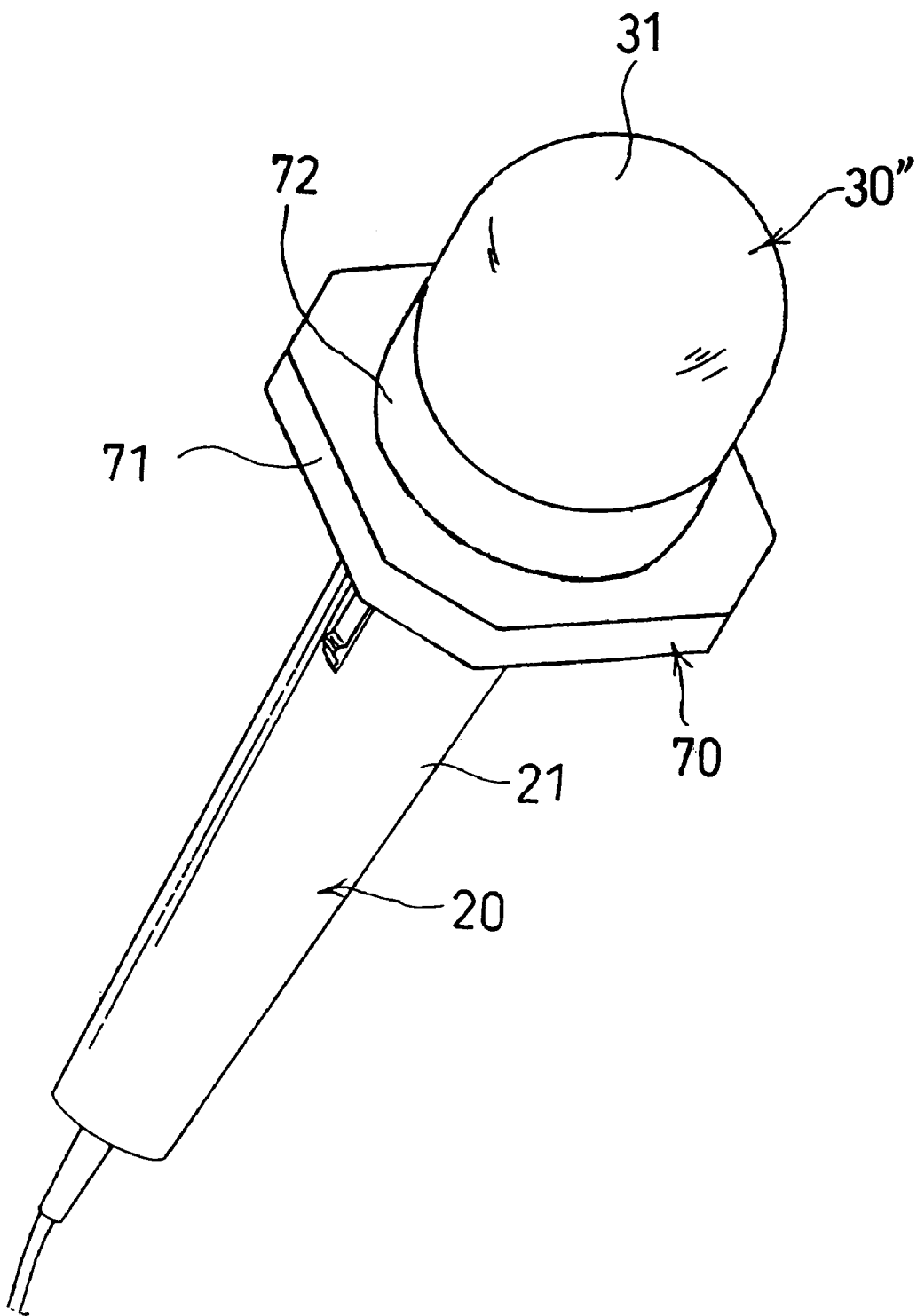
FIG. 20 is a perspective view of a microphone, the head of which is covered by yet another embodiment of the antibacterial deodorant microphone cover.
Figure 21:
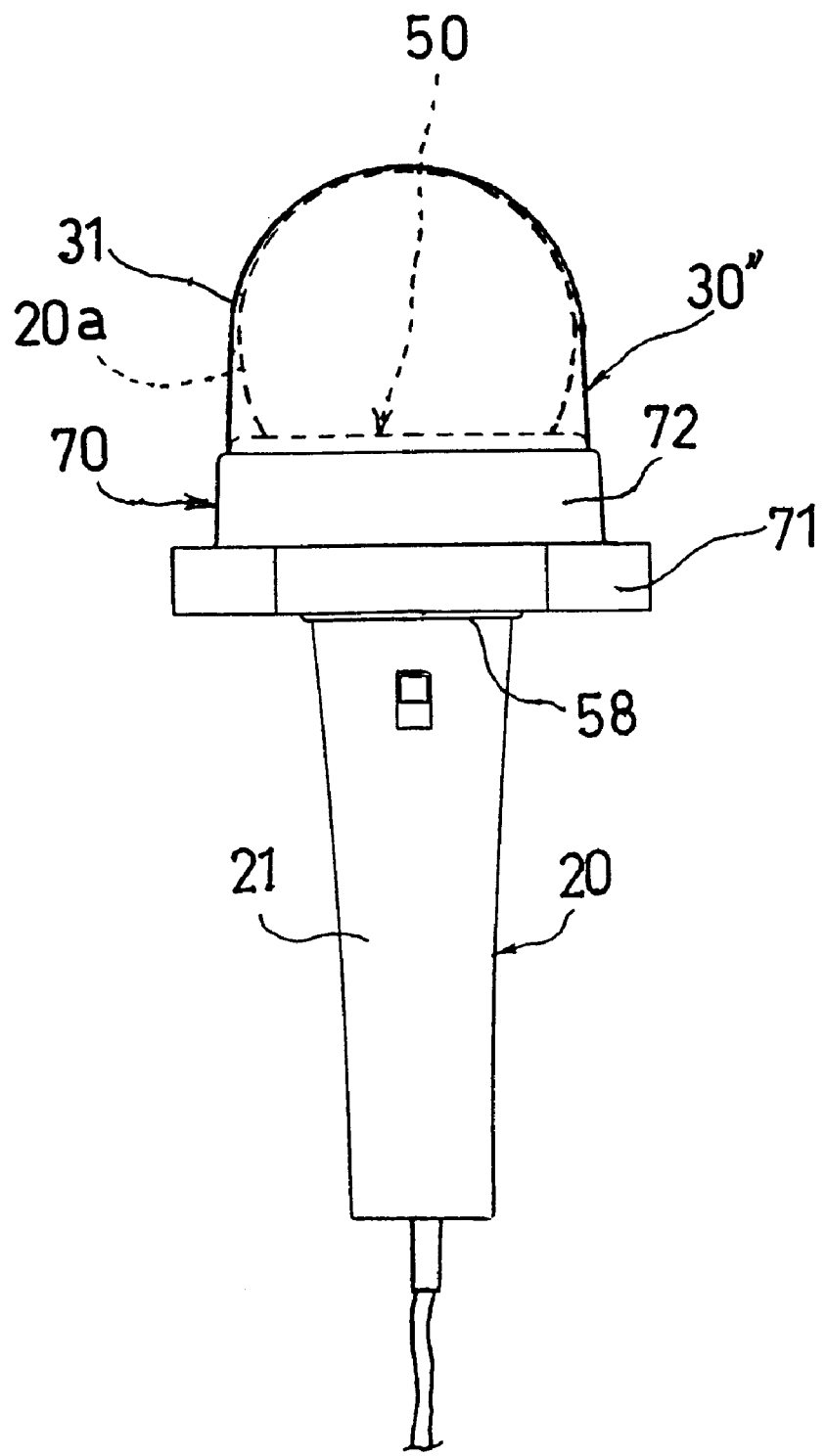
FIG. 21 is a front view of the microphone shown in FIG. 20.

FIGS. 14 to 19 show the sixth embodiment of the present invention of the antibacterial deodorant microphone cover. In this embodiment, an antibacterial deodorant microphone cover 30' is fixed to a retainer 35' without utilizing double-sided tape or VELCRO as a fixing device. Namely, a skirt portion 32 of the microphone cover 30' is fixed to the retainer 35 using an annular fixing member 40 capable of being fitted on the periphery of the retainer 35'. The microphone cover 30' is identical to the microphone cover 30 except that the four corners of the skirt portion 32 are cut off, as can be seen in FIGS. 14 and 15. Similarly, the retainer 35' used herein is identical to the retainer 35 except that the four corners thereof are cut off in conformity with the shape of the microphone cover 30'.

The annular fixing member 40 is a molded product made of a flexible plastic (e.g., polypropylene), and is constituted so that the annular fixing member 40 can be fitted on the periphery of the retainer 35'. As is illustrated, the annular fixing member 40 is constituted from a ring-shaped upper wall 41 to be opposed to an upper surface of the retainer 35' having been fitted on the grip 21 of the microphone 20, a ring-shaped peripheral wall 42 extending from an outer edge of the ring-shaped upper wall 41 in a direction substantially perpendicular to the upper wall 41, and four engaging projections 43 each inwardly extending from a lower end of the ring-shaped peripheral wall 42 (see FIGS. 18 and 19).

The ring-shaped upper wall 41 has an opening 44 formed in a central portion thereof. A diameter of the opening 44 is substantially the same as the maximum diameter of the covering portion 31 of the microphone cover 30'. Each engaging projection 43 extends inwardly from a lower end of the ring-shaped peripheral wall 42 in a direction substantially parallel to the ring-shaped upper wall 41.

To fix the microphone cover 30' to the retainer 35', the microphone cover 30' is first put on the head of the microphone 20 with the covering portion 31 of the microphone cover 30' covering the head of the microphone 20. Subsequently, the annular fixing member 40 is put on the skirt portion 32 of the microphone cover 30' with the inner surface of the ring-shaped upper wall 41 contacting the skirt portion 32 as shown in FIG. 14. Thereafter, the retainer 35' is fitted on the grip 21 of the microphone 20 by inserting the grip 21 into the circular hole 36 from the lower end of the grip 21. The retainer 35' is fitted in the inner side of the annular fixing member 40 against an elastic force of each engaging projection 43. Once the retainer 35' is positioned in the inner side of the annular fixing member 40, the engaging projections 43 prevent the annular fixing member 40 from easily coming off the retainer 35'.

FIG. 14 illustrates a way of fitting the retainer 35' in the annular fixing member 40. When it is securely fitted in the inner side of the annular fixing member 40, the circular surface 37 of the retainer 35' tightly contacts an upper approximate end of the grip 21 of the microphone 20 under the head thereof. In this state the retainer 35' is held between the ring-shaped upper wall 41 and the engaging projections 43, while the skirt portion 32 of the microphone cover 30' is held between the upper surface of the retainer 35' and the ring-shaped upper wall 41. Thus, the fixing process of the microphone cover 30' to the retainer 35' is now completed.

In the above sixth embodiment of the microphone cover, if the annular fixing member 40 has a cushioning material such as rubber at least along a peripheral portion of the annular fixing member 40, the above-mentioned problem concerning a loud and undesirable noise generated upon the head of the microphone making contact with the table, for example, can be effectively avoided. Alternatively, a similar effect will be obtained if any cushioning material such as rubber is fixed to a peripheral part of the ring-shaped peripheral wall 42.

Furthermore, in the above-mentioned sixth embodiment, the annular fixing member 40 is a molded product made of a flexible plastic material. However, the annular fixing member 40 may be made of any other material such as a metal. When a metal or the like is used to make the annular fixing member 40, it is preferred that at least the engaging projections 43 be made of a flexible material so that the retainer 35' can be easily inserted and fitted in the annular fixing member 40. However, when the retainer 35' itself is made of a cushioning material such as rubber, the engaging projections 43 may be constituted from any material having no flexibility, because the retainer 35' can be inserted and fitted in the annular fixing member 40 after its deformation.

Furthermore, in the practice of the present invention, a configuration of the peripheral portion of the annular fixing member 40 and the retainer 35' is not restricted to those of the above-discussed embodiments. Any other configuration may be used, as long as the annular fixing member 40 can be suitably fitted in the retainer 35' after having been inserted in the annular fixing member 40.

Figure 22:
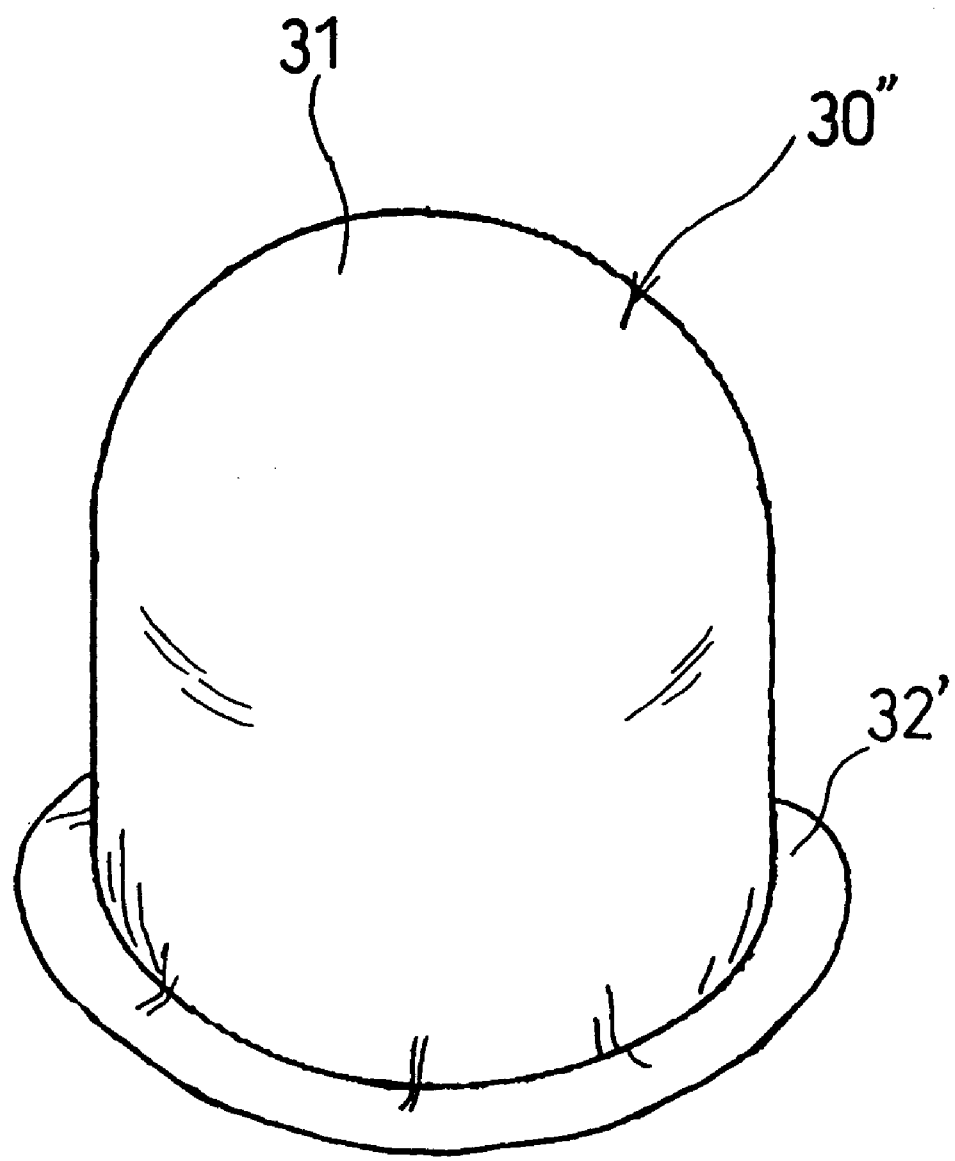
FIG. 22 is a perspective view of the antibacterial deodorant microphone cover shown in FIGS. 20 and 21.

FIGS. 20 to 38 show the seventh embodiment of the present invention of the antibacterial deodorant microphone cover. In the seventh embodiment, an antibacterial deodorant microphone cover 30" as shown in FIG. 22 is fixed to the head of the microphone 20. The antibacterial deodorant microphone cover 30" is identical to the aforementioned antibacterial deodorant microphone cover 30' shown in FIG. 15 except that the aforementioned antibacterial deodorant microphone cover 30' is provided with the octognoal skirt portion 32 while the antibacterial deodorant microphone cover 30" is provided with a skirt portion 32' having a substantially circular edge.

In the seventh embodiment, the fixing device for fixing the antibacterial deodorant microphone cover 30" to the head of the microphone 20 is composed a first annular member 50 detachably fixed to the neck of the grip 21, i.e., an approximate top end of the grip 21, and a second annular member 70 detachably fitted on the first annular member 50.

FIGS. 23 through 31 show the first annular member 50. The first annular member 50 is a molded product made of a flexible plastic (e.g., polypropylene). The first annular member 50 is provided with a pair of first and second semi-cylindrical members (i.e., semi-cylindrical pieces) 51 and 52 which are formed substantially symmetrical to each other.

Figure 23:
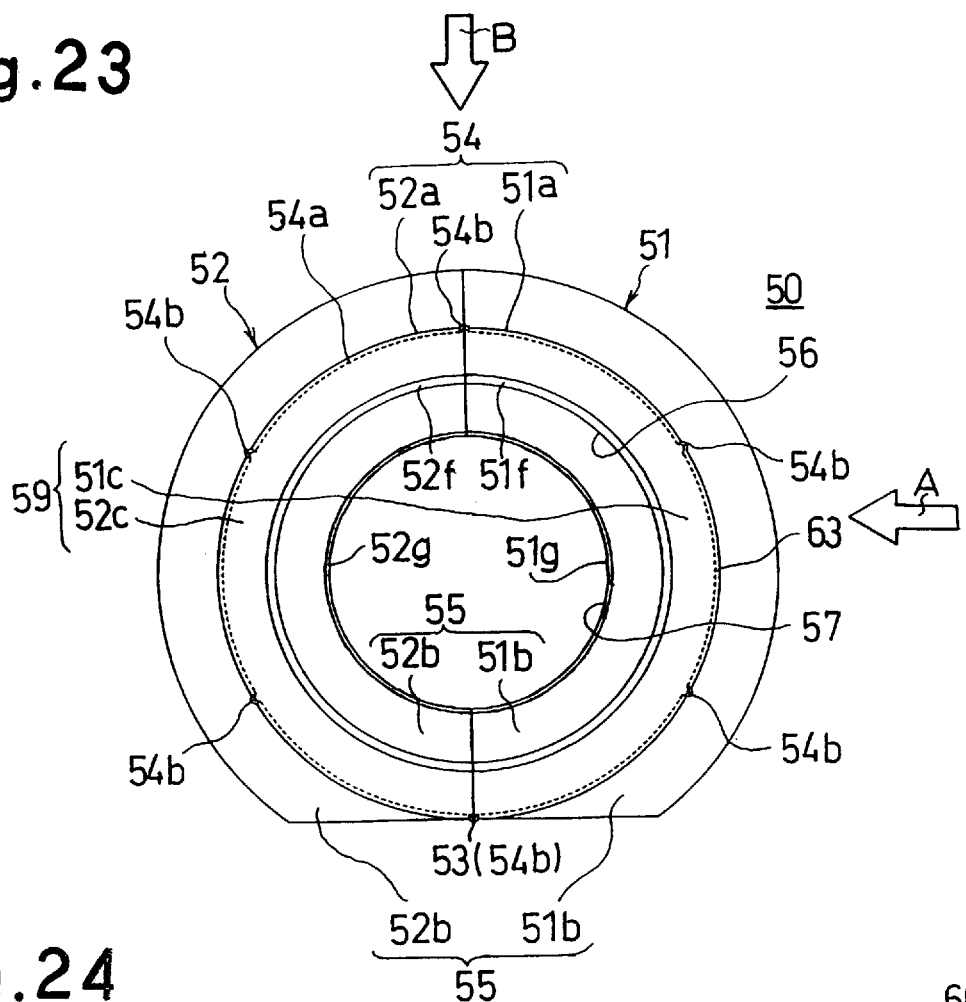
FIG. 23 is a plan view of a first annular member in a closed state.
Figure 24:
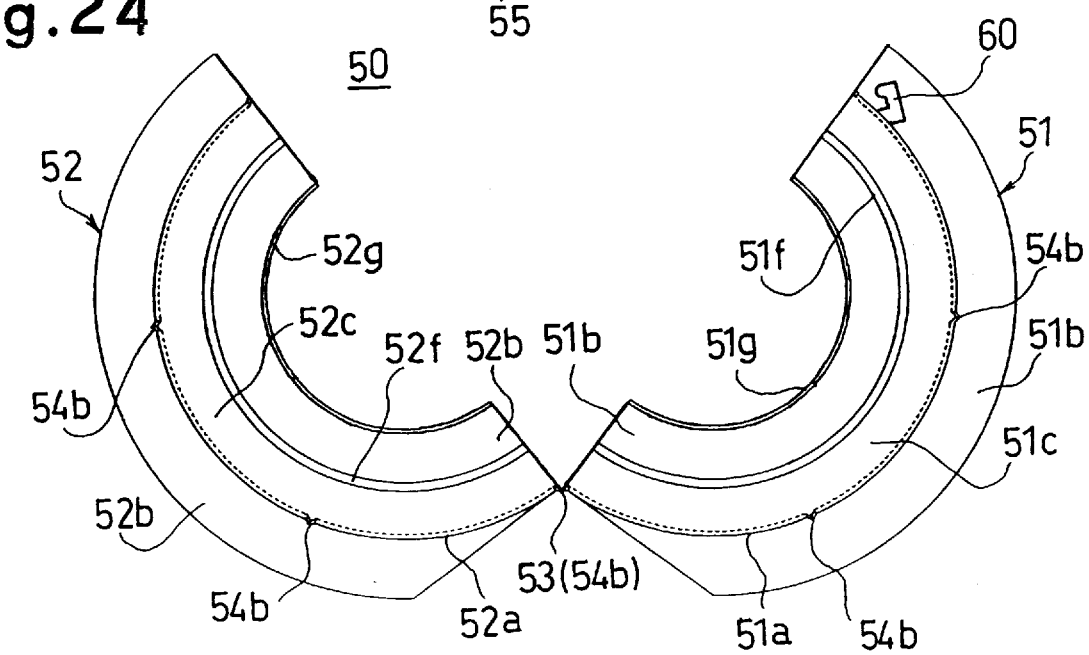
FIG. 24 is a plan view of the first annular member in an opened state.
Figure 25:
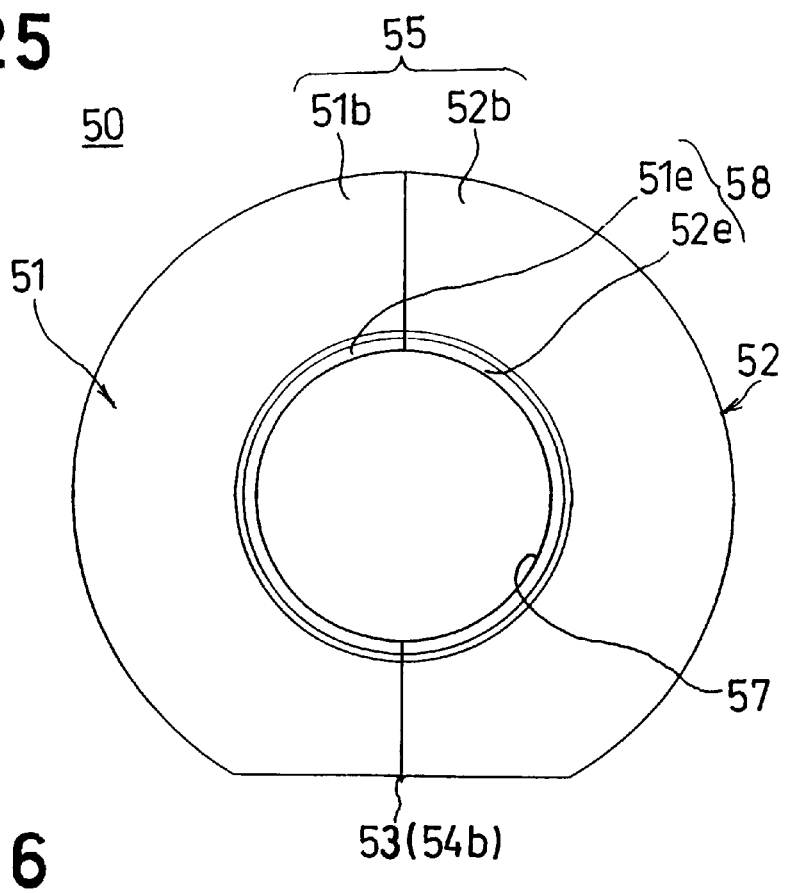
FIG. 25 is a bottom view of the first annular member shown in FIG. 23.
Figure 26:
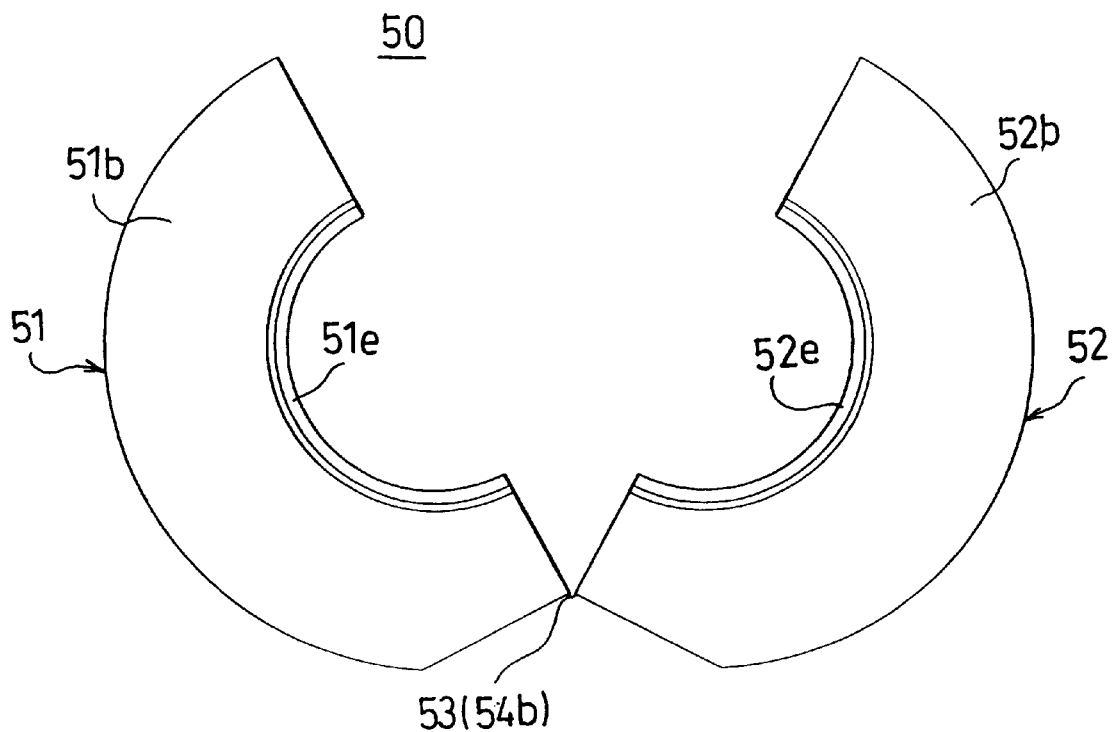
FIG. 26 is a bottom view of the first annular member shown in FIG. 24.
Figure 27:
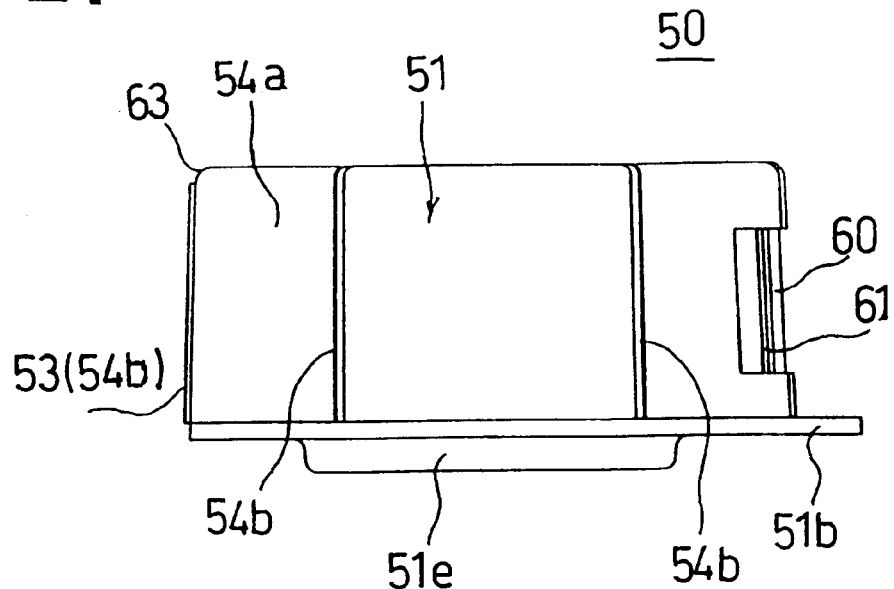
FIG. 27 is a side view of the first annular member as viewed in the direction of arrow A of FIG. 23.

The first annular member 50 is provided between the first and second semi-cylindrical members 51 and 52 with a thin flexible portion 53 which extends substantially in an axial direction of the first annular member 50, i.e., a direction perpendicular to the surface of FIG. 23 or a vertical direction of FIG. 27. The flexible portion 53 is formed integral with the first and second semi-cylindrical members 51 and 52 to connect these to each other. The flexible portion 53 functions like a hinge, so that the first and second semi-cylindrical members 51 and 52 can be opened or closed at the flexible portion 53 therealong. FIGS. 23, 25, 27, 28 and 30 show a state where the first and second semi-cylindrical members 51 and 52 are closed, while FIGS. 24, 26, 29 and 31 show another state where the first and second semi-cylindrical members 51 and 52 are open. As can be seen from FIGS. 23, 27 and 28, the first annular member 50 is in a substantially single cylindrical shape in its closed state where the first and second semi-cylindrical members 51 and 52 are closed.

The first semi-cylindrical member 51 is provided with a semi-cylindrical portion 51a and a semi-circular plate 51b fixed to a lower end (i.e., a lower end as viewed in FIG. 27 or 28) of the semi-cylindrical portion 51a. Similarly, the second semi-cylindrical member 52 is provided with a semi-cylindrical portion 52a and a semi-circular plate 52b fixed to a lower end (i.e., a lower end as viewed in FIG. 27 or 28) of the semi-cylindrical portion 52a. The semi-cylindrical portions 51a and 52a together form a cylindrical portion (i.e., inner cylindrical portion) 54 in the state where the first and second semi-cylindrical members 51 and 52 are closed. The semi-circular plates 51b and 52b together form a circular plate portion 55 in the state where the first and second semi-cylindrical members 51 and 52 are closed.

Figure 28:
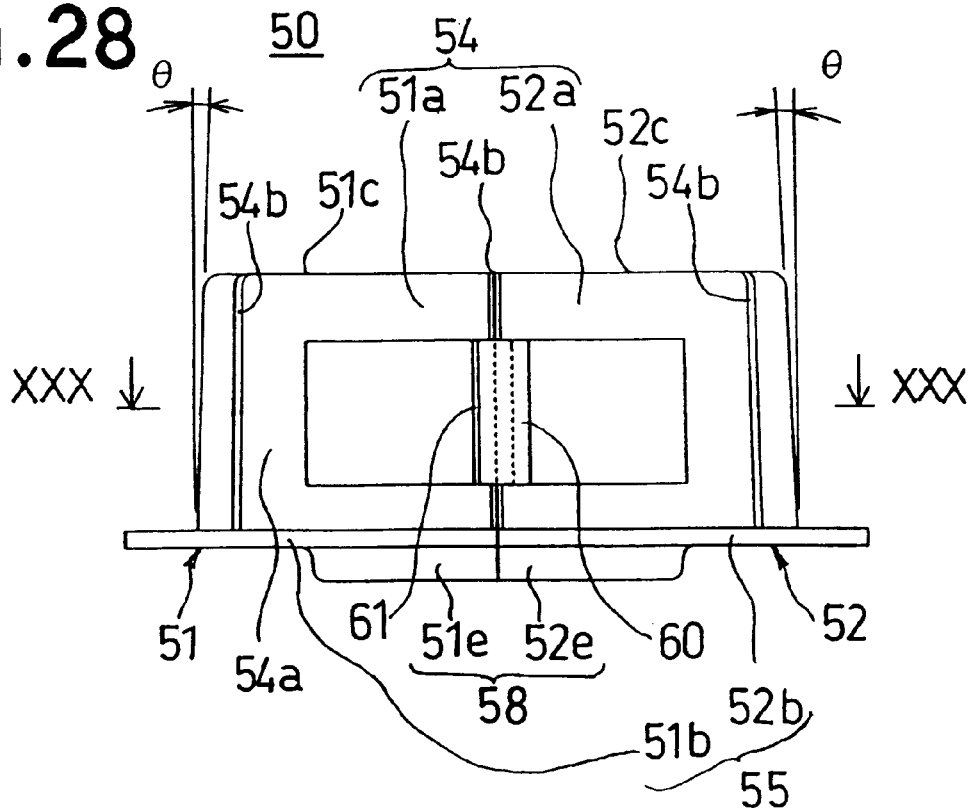
FIG. 28 is a side view of the first annular member as viewed in the direction of arrow B of FIG. 23.
Figure 29:
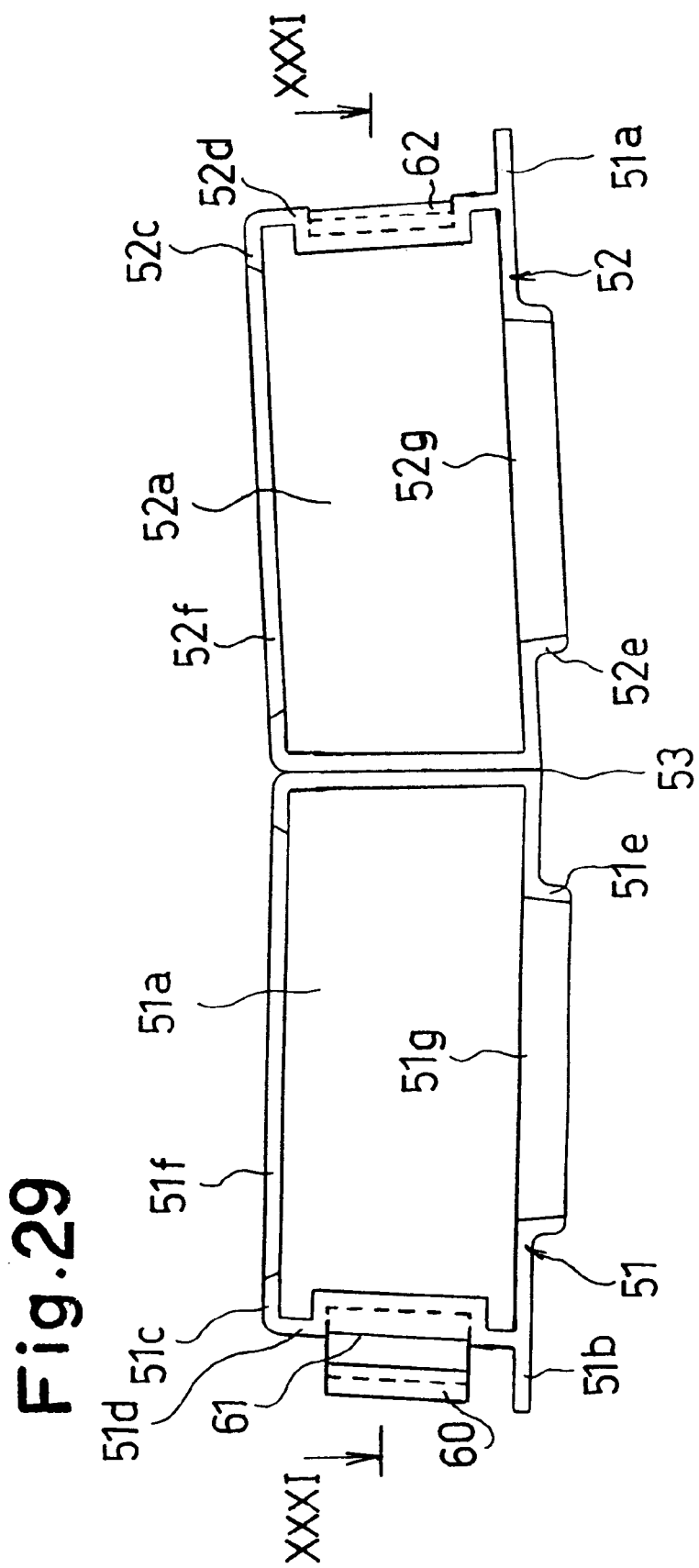
FIG. 29 is an inside view of the first annular member in a opened state.

The outer peripheral surface 54a of the cylindrical portion 54, i.e., the outer peripheral surface of each of the semi-cylindrical portions 51a and 52a, is formed to taper away from the circular plate portion 55. The outer peripheral surface 54a of the cylindrical portion 54 is angled relative to the axial direction of the first annular member 50 by a predetermined angle θ. The angle θ shown in FIG. 28 is set to be about two degrees (2°).

The outer peripheral surface 54a of the cylindrical portion 54, i.e., the outer peripheral surface of each of the semi-cylindrical portions 51a and 52a, is provided with a plurality of ribs or projections 54b each extending substantially parallel to the axial direction of the first annular member 50. The plurality of ribs 54b are formed on the outer peripheral surface 54a at substantially regular intervals, and each rib 54b projects from the outer peripheral surface 54a by a small amount, about 0.3 to 0.4 mm. The outer surface of the thin flexible portion 53 slightly projects from the outer peripheral surface 54a by a small amount substantially identical to that of each rib 54b when the first and second semi-cylindrical members 51 and 52 are in a closed state so that the projecting outer surface portion of the thin flexible portion 53 forms one of the plurality of ribs 54b (see FIG. 23).

The semi-cylindrical portion 51a is provided at an upper end thereof (i.e., an upper end as viewed in FIG. 27 or 28) with a semi-circular flange 51c which inwardly extends normal to the semi-cylindrical portion 51a. Likewise, the semi-cylindrical portion 52a is provided at an upper end thereof (i.e., an upper end as viewed in FIG. 27 or 28) with a semi-circular flange 52c which inwardly extends normal to the semi-cylindrical portion 52a. The semi-circular flanges 51c and 52c together form an inward flange 59 formed at the upper end of the cylindrical portion 54. Inside edges 51f and 52f of the semi-circular flanges 51c and 52c together form an upper circular opening 56 when the first and second semi-cylindrical members 51 and 52 are in a closed state.

An upper circular edge 63 of the cylindrical portion 54 (see FIGS. 23 and 27) is rounded off so that a peripheral portion of the microphone cover 30" can be easily fitted on the cylindrical portion 54.

Inside edges 51g and 52g of the semi-circular plates 51b and 52b together form a lower circular opening 57 when the first and second semi-cylindrical members 51 and 52 are in a closed state. The semi-circular plates 51b and 52b are provided with projections 51e and 52e which extend from the inside edges 51g and 52g in a direction away from the upper circular opening 56, respectively. The projections 51e and 52e together form a circular projection 58 in the state where the first and second semi-cylindrical members 51 and 52 are closed.

Figure 30:
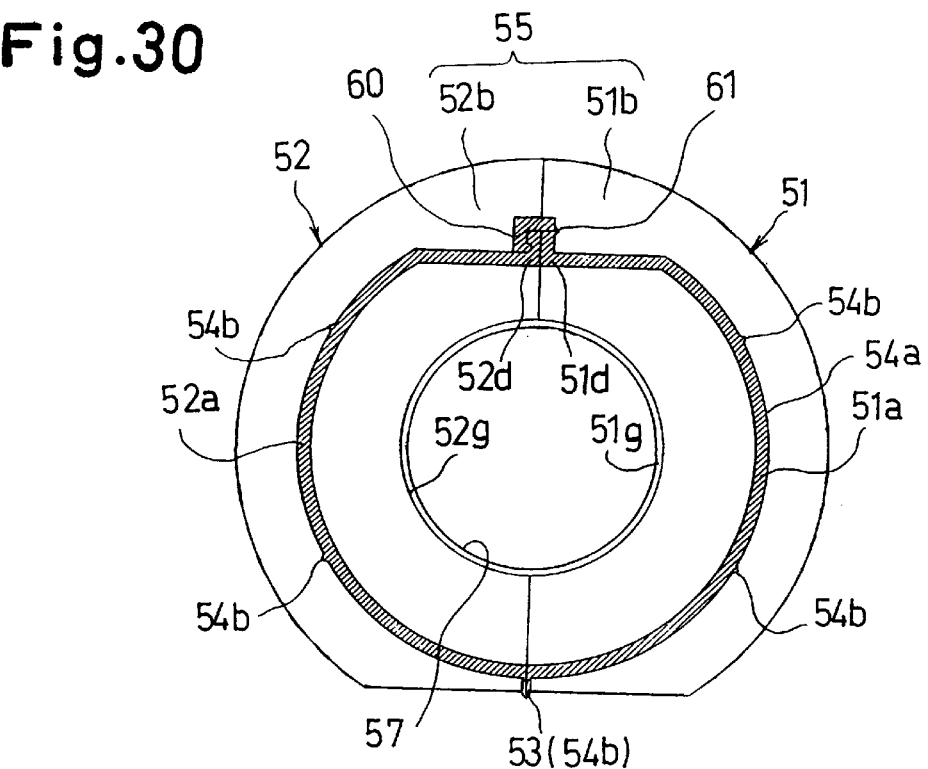
FIG. 30 is an cross-sectional view of the first annular member taken along line XXX—XXX of FIG. 28.
Figure 31:
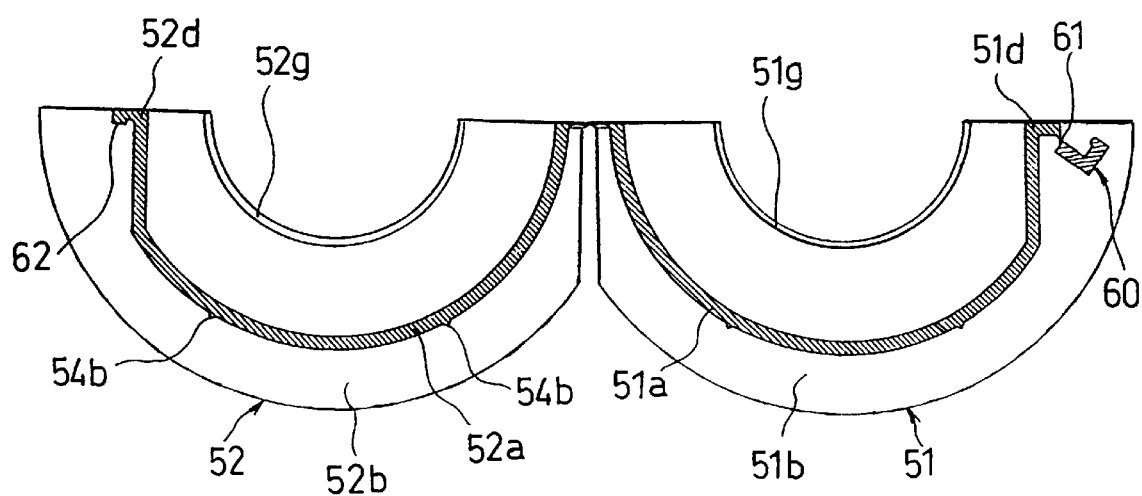
FIG. 31 is a cross-sectional view of the first annular member taken along line XXXI—XXXI of FIG. 29.
Figure 32:
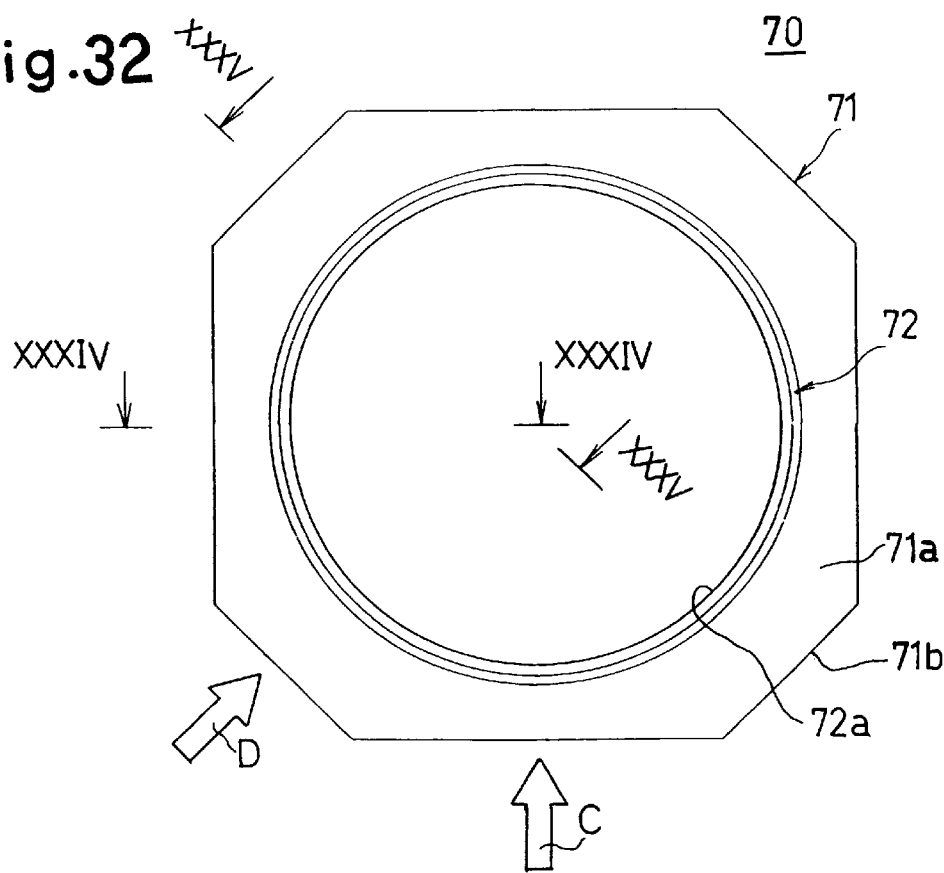
FIG. 32 is a plan view of a second annular member.
Figure 33:
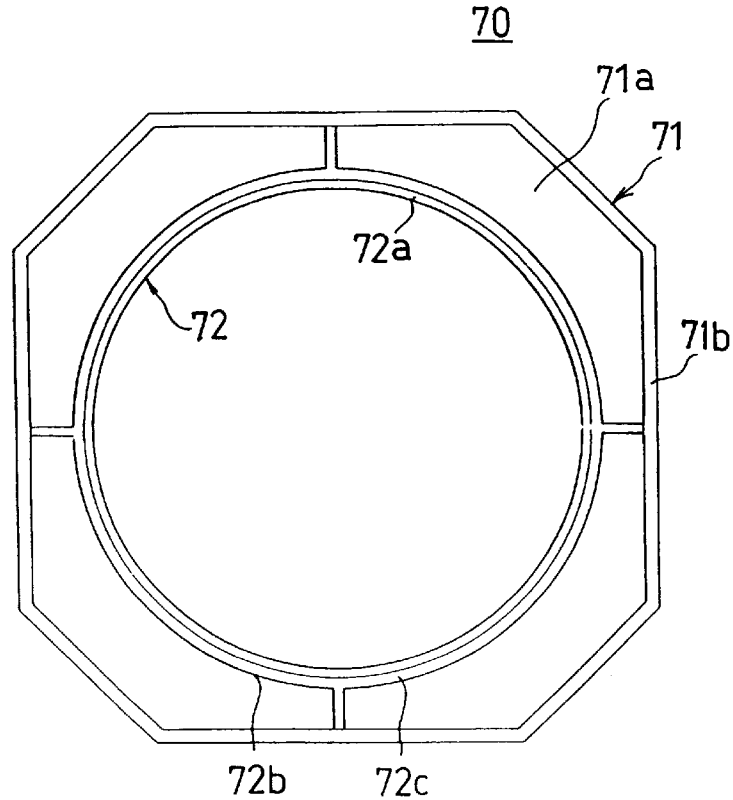
FIG. 33 is a bottom view of the second annular member of FIG. 32.

A free end 51d of the semi-cylindrical portion 51a is provided with a movable engaging piece 60 having a substantially "L" shape in a cross-sectional view. The engaging piece 60 is connected to the free end 51d through a thin flexible portion 61 which is formed integral with both the engaging piece 60 and the free end 51d, and which extends substantially in the axial direction of the first annular member 50, so that the engaging piece 60 can be rotated about the flexible portion 61. A free end 52d of the semi-cylindrical portion 52a is provided with an engaging portion 62 (see FIGS. 29 and 31) with which the engaging piece 60 can engage under the condition that the first and second semi-cylindrical members 51 and 52 are closed. Accordingly, the engaging piece 60 can engage with the engaging portion 62 when the first and second semi-cylindrical members 51 and 52 are in a closed state as shown in FIG. 30, and the first and second semi-cylindrical members 51 and 52 are prevented from being opened when the engaging piece 60 engages with the engaging portion 62. The engaging piece 60, the thin flexible portion 61, the engaging portion 62, etc. together constitute a locking device for preventing the semi-cylindrical pieces 51 and 52 from being opened.

Figure 38:
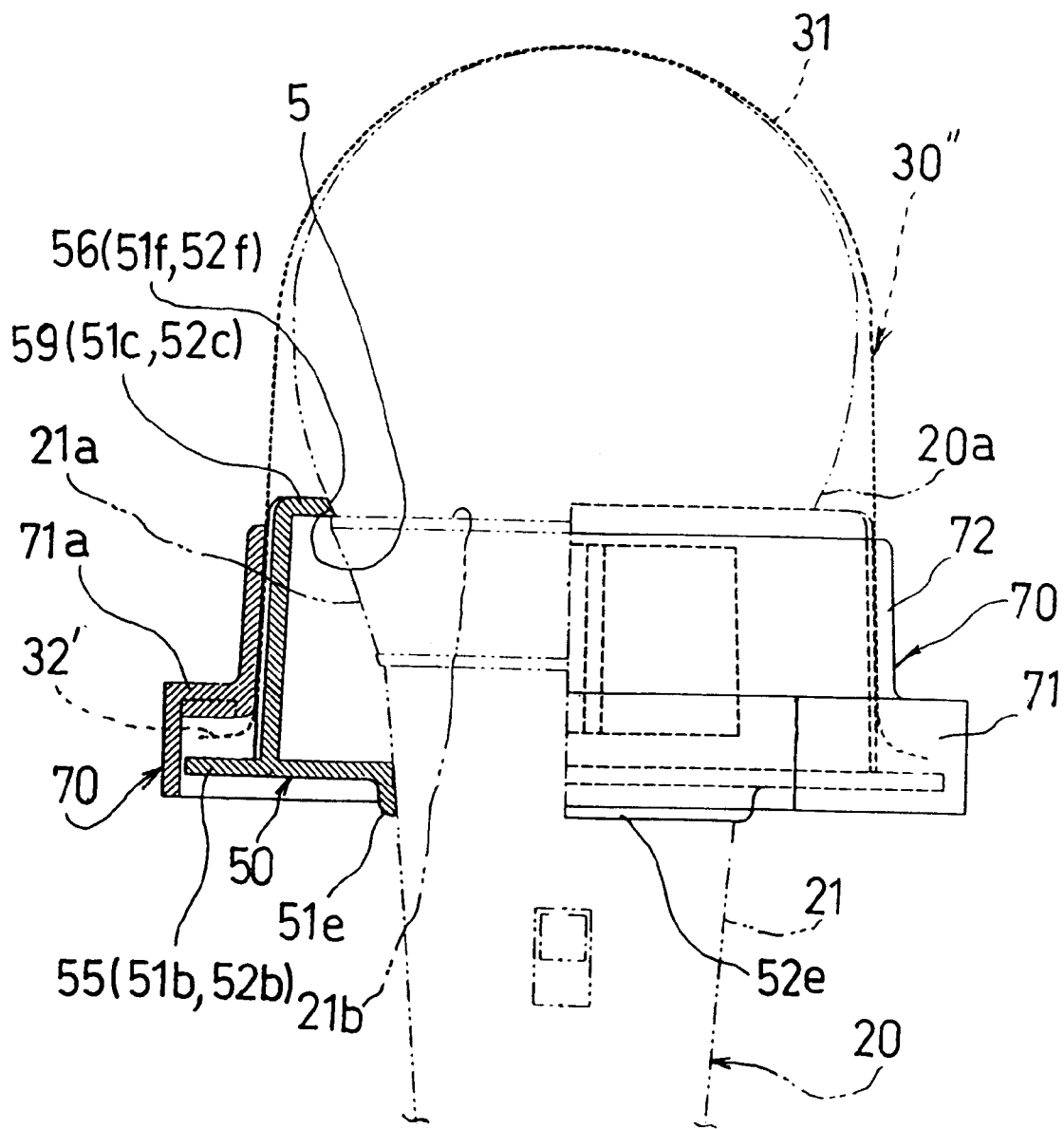
FIG. 38 is a cross-sectional view of the first annular member, the second annular member and the antibacterial deodorant microphone cover shown in FIG. 22 properly fixed to the head of a microphone using the first and second annular members.

As shown in FIG. 38, the microphone 20 is provided at the top of the grip 21 with a connecting ring 21a which connects the head 20a of the microphone 20 to the top of the grip 21. The first annular member 50 having the aforementioned structure is manually fixed to the microphone 20 around the neck thereof, i.e., the approximate top end of the grip 21. In the process of fixing the first annular member 50 to the microphone 20, the neck of the grip 21 is placed between the first and second semi-cylindrical members 51 and 52 after the first and second semi-cylindrical members 51 and 52 are opened, and subsequently the first and second semi-cylindrical members 51 and 52 are closed to engage the engaging piece 60 with the engaging portion 62, which completes the process of fixing the first annular member 50 to the neck of the microphone 20.

In the aforementioned procedure of fixing the first annular member 50 to the microphone 20, the inside edges 51f and 52f of the semi-circular flanges 51c and 52c are brought into tight contact with an annular gap 5 formed on the microphone 20 between the upper rim 21b of the connecting ring 21a and the outer peripheral surface of the head 20a, and at the same time the projections 51e and 52e are brought into tight contact with a circumference of the grip 21 in the vicinity of the lower rim of the connecting ring 21a.

Accordingly, the diameter of the upper circular opening 56, which is formed by the inside edges 51f and 52f of the semi-circular flanges 51c and 52c, is predetermined to be substantially identical to that of the annular gap 5 so that the inside edges 51f and 52f can be tightly fitted on and around the annular gap 5. Similarly, the diameter of the lower circular opening 57, which is formed by the inner surfaces of the projections 51e and 52e, i.e., by the inner surface of the circular projection 58, is predetermined to be substantially identical to that of the corresponding circumference of the grip 21 so that the inner surface of the circular projection 58 can be tightly fitted on and around the corresponding circumference of the grip 21.

The inner surface of the circular projection 58, which contacts the corresponding circumference of the grip 21, is formed to taper toward the lower end of the grip 21 so as to be capable of being tightly fitted on the tapered grip 21. Due to a similar reason, the inside edges 51f and 52f of the semi-circular flanges 51c and 52c are formed to taper toward the lower end of the grip 21 to be capable of being tightly fitted on the tapered circumference of the head 20a at the annular gap 5. The engagement of the inside edges 51f and 52f with the annular gap 5 prevents the first annular member 50 from coming off the grip 21, i.e., from shifting toward the lower end of the grip 21.

FIGS. 32 through 35 show the second annular member 70. The second annular member 70 is a molded product made of a flexible plastic (e.g., polypropylene). The second annular member 70 is provided with an annular base portion 71 having a shape similar to that of the aforementioned annular fixing member 40, and a cylindrical portion (i.e., outer cylindrical portion) 72 integrally formed on the annular base portion 71 at the center thereof. The cylindrical portion 72 is fitted on the cylindrical portion 54 of the first annular member 50 when the second annular member 70 is fitted on the first annular member 50.

An inner peripheral surface 72a of the cylindrical portion 72 is formed to taper away from the annular base portion 71 and is angled relative to the axial direction of the first annular member 50 by a predetermined angle substantially identical to the aforementioned angle θ of the outer peripheral surface 54a. Accordingly, when the cylindrical portion 72 is fitted on the cylindrical portion 54, the outer peripheral surface 54a and the inner peripheral surface 72a are parallel to each other. Further, when the cylindrical portion 72 is directly fitted on the cylindrical portion 54, a slight gap is formed between the outer peripheral surface 54a and the inner peripheral surface 72a. Accordingly, the diameter of the inner peripheral surface 72a is predetermined so that the cylindrical portion 72 is fitted on the cylindrical portion 54 while forming the slight gap between the cylindrical portion 54 and the cylindrical portion 72. A peripheral portion of the microphone cover 30" is positioned in the aforementioned slight gap formed between the outer peripheral surface 54a and the inner peripheral surface 72a when the microphone cover 30" is properly fixed to the head 20a of the microphone 20 by using the first and second annular members 50 and 70.

The annular base portion 71 is provided with an annular upper wall 71a and a circumferential wall 71b which extends normal from the circumferential edge of the annular upper wall 71a. The circular plate portion 55 of the first annular member 50 is positioned inside the circumferential wall 71b when the cylindrical portion 72 is fitted on the cylindrical portion 54.

Figure 34:
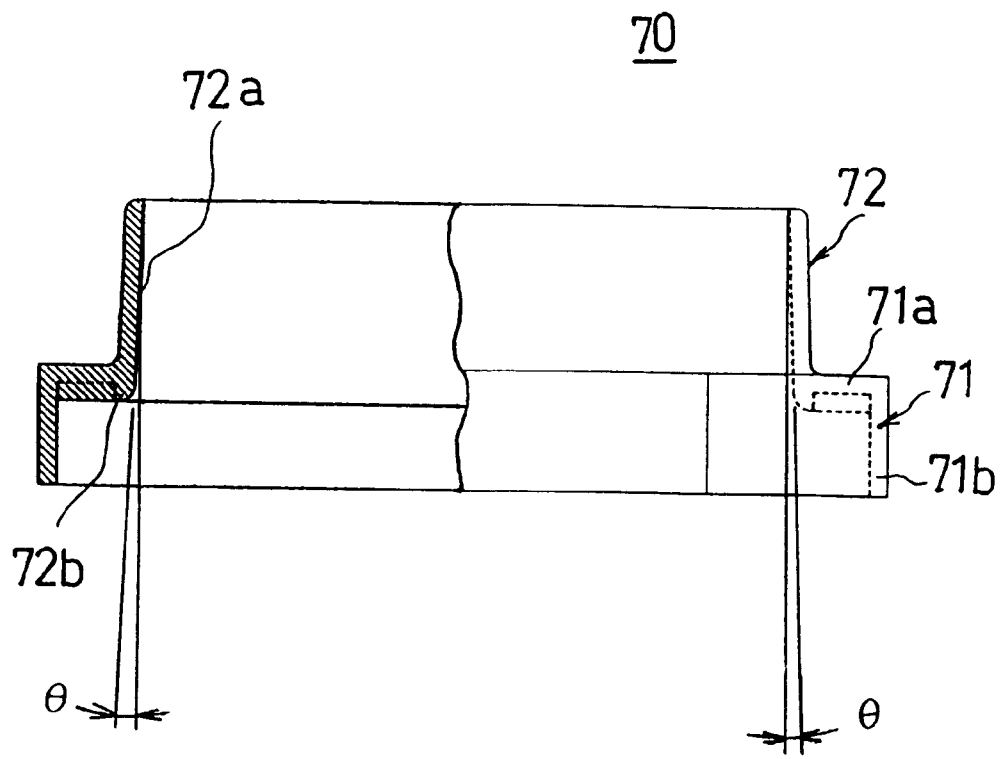
FIG. 34 is a side view of the second annular member as viewed in the direction of arrow C of FIG. 32, in which about a half of the second annular member is shown as a cross-sectional view taken along line XXXIV—XXXIV of FIG. 32.
Figure 35:
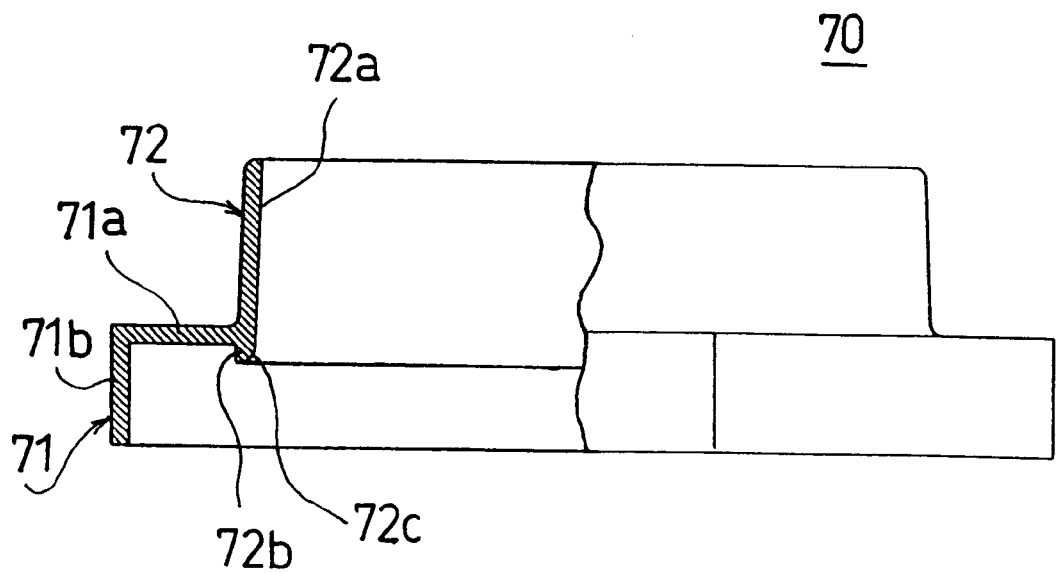
FIG. 35 is a side view of the second annular member as viewed in the direction of arrow D of FIG. 32, in which about a half of the second annular member is shown as a cross-sectional view taken along line XXXV—XXXV of FIG. 32.
Figure 36:
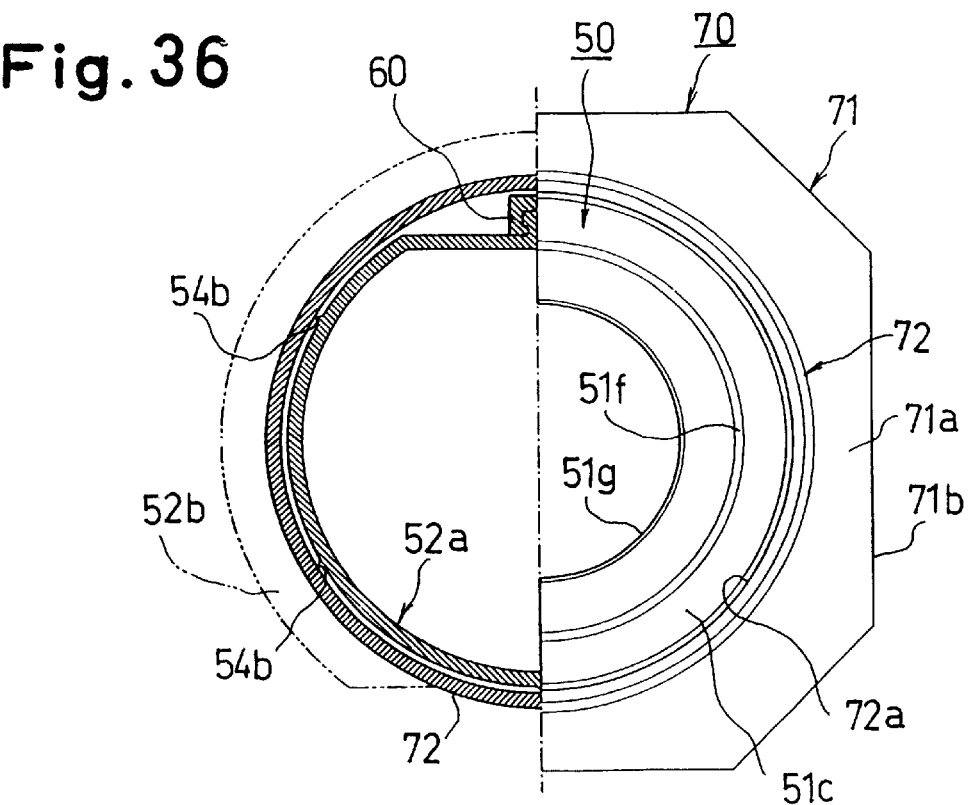
FIG. 36 is a plan view of the first annular member and the second annular member with the second annular member properly fitted on the first annular member, showing a state of engagement of an inner cylindrical portion of the first annular member with an outer cylindrical portion of the second annular member in a cross-section.
Figure 37:
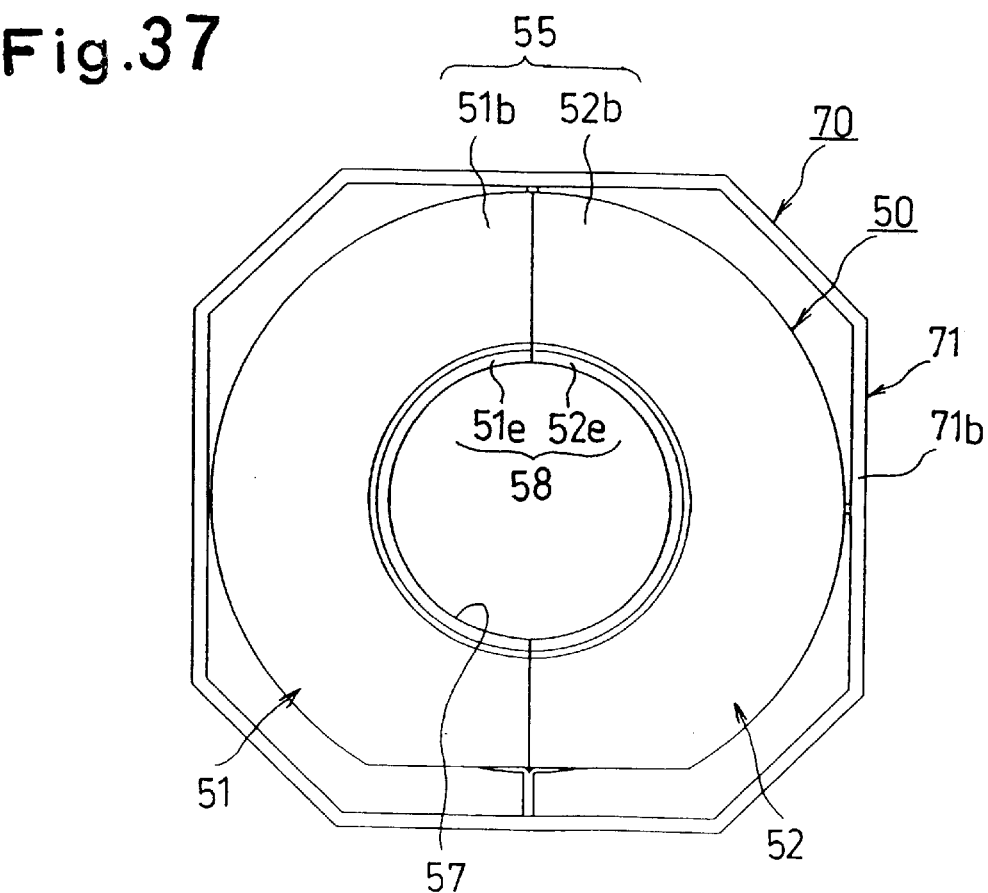
FIG. 37 is a bottom view of the first annular member and the second annular member with the second annular member properly fitted on the first annular member.

As shown in FIGS. 34 and 35, the lower end of the cylindrical portion 72 is formed as an annular lip portion 72b which extends downwardly as viewed in FIG. 35 from the annular upper wall 71a. The inner peripheral surface 72c of the annular lip portion 72b, i.e., the lower end surface of the inner peripheral surface 72a, is formed to taper toward the annular upper wall 71a so that the cylindrical portion 72 can be easily fitted on the cylindrical portion 54.

The microphone cover 30" is fixed to the head 20a of the microphone 20 by using the first and second annular members 50 and 70 in the following manner.

First, the first annular member 50 is appropriately fixed to the neck of the grip 21 in the aforementioned manner. Subsequently, the microphone cover 30" is put on the head 20a of the microphone 20. In this procedure of putting the microphone cover 30" on the head 20a, the head 20a is covered with the covering portion 31 and at the same time the peripheral portion of the microphone cover 30" which includes the skirt portion 32', is fitted on the cylindrical portion 54 of the first annular member 50. The inner diameter of the peripheral portion of the microphone cover 30" is predetermined to be slightly larger but substantially identical to the diameter of the outer peripheral surface 54a of the cylindrical portion 54 so that the peripheral portion of the microphone cover 30" can be fitted on the outer peripheral surface 54a of the cylindrical portion 54.

Thereafter, the second annular member 70 is fitted on the first annular member 50, i.e., the cylindrical portion 72 is fitted on the cylindrical portion 54 with the circular plate portion 55 positioned inside the circumferential wall 71b. In this procedure of fitting the second annular member 70 on the first annular member 50, the second annular member 70 is manually pushed against the first annular member 50 toward the lower end of the microphone 20 so as to tightly fit the cylindrical portion 72 on the cylindrical portion 54, which causes a peripheral portion of the microphone cover 30" to be tightly held between the cylindrical portions 54 and 72 with the skirt portion 32' positioned between the annular upper wall 71a and the peripheral part of the circular plate portion 55, which completes the process of fixing the microphone cover 30" to the neck of the microphone 20. In this state, the microphone cover 30" is tightly held between the cylindrical portions 54 and 72, especially between the inner peripheral surface 72a of the cylindrical portion 72 and each of the plurality of ribs 54b. When it is desired to take the microphone cover 30" off the head 20a, the microphone cover 30" can be easily taken off after the second annular member 70 is taken off the first annular member 50, so that the microphone cover 30" can be easily replaced with a new one.

When the cylindrical portion 72 is fitted on the cylindrical portions 54 after the peripheral portion of the microphone cover 30" has been fitted on the cylindrical portions 54, the skirt portion 32' is pushed toward the circular plate portion 55 by the annular upper wall 71a to be located at an appropriate position between the annular upper wall 71a and the peripheral part of the circular plate portion 55 even if the peripheral portion of the microphone cover 30" was initially not fitted deeply enough on the cylindrical portions 54. Therefore, whenever the cylindrical portion 72 is fitted on the cylindrical portions 54 after the peripheral portion of the microphone cover 30" has been fitted on the cylindrical portions 54, the peripheral portion of the microphone cover 30" is properly fitted on the cylindrical portions 54 to be held between the cylindrical portion 72 and the cylindrical portions 54.

In the seventh embodiment, the second annular member 70 is made of a flexible plastic, but the circumferential wall 71b may be made of a cushioning member such as rubber. With this structure, even when the microphone 20 is carelessly placed on a table or the like with the switch of the microphone 20 remaining ON, the aforementioned loud and undesirable noise is effectively prevented from occurring, or reduced to be almost negligible. A cushioning member such as rubber may be fixed to the circumference of the circumferential wall 71b to obtain a similar effect.

The diameter of the upper circular opening 56, which is formed by the inner circumferential end of the inward flange 59, and the diameter of the lower circular opening 57, which is formed by the inner circumferential end of the circular plate portion 55, are each selectively determined to correspond to the diameter of the corresponding circumference of the neck of the microphone 20 to be used.

In the seventh embodiment, although the microphone cover 30" is provided with the skirt portion 32' which extends outwardly from the rim of the covering portion 31, the microphone cover 30" may be formed without having the skirt portion 32'. This is because the peripheral portion of the microphone cover 30" is properly and tightly held between the cylindrical portion 72 and the cylindrical portions 54 when the cylindrical portion 72 is fitted on the cylindrical portions 54 as long as the peripheral portion of the microphone cover 30" is properly fitted on the cylindrical portions 54 before the second annular member 70 is fitted on the first annular member 50.

In the seventh embodiment, the flexible portion 53 may be replaced with a hinge so that the first and second semi-cylindrical members 51 and 52 can be opened or closed at the hinge.

Obvious changes may be made in the specific embodiments of the present invention described herein, such modifications being within the spirit and scope of the invention claimed. It is indicated that all matter contained herein is illustrative and does not limit the scope of the present invention.

We claim:

1. A deodorant cover for a microphone, comprising:
   a matrix member comprising nonwoven fabric having a predetermined configuration which corresponds to a head of a microphone, wherein said matrix member carries a calcium phosphate compound having a Ca/P ratio in a range of about 1.0 to 2.0; and
   a fixing element for fixing said matrix member to the head of the microphone.

2. The deodorant cover of claim 1, wherein said calcium phosphate compound comprises particles having an average particle diameter in a range of about 0.1 to 100 microns.

3. The deodorant cover of claim 1, wherein said matrix member has a pattern printed thereon.

4. The deodorant cover of claim 1, wherein said predetermined configuration corresponds to a substantially spherical surface of said head of said microphone.

5. A method for associating a matrix member to a microphone head, comprising:
   providing a microphone comprising a microphone head;
   providing a matrix member having a configuration corresponding to said microphone head, wherein said matrix member carries a calcium phosphate compound having a Ca/P ratio in a range of about 1.0 to 2.0; and
   fixing said matrix member over said microphone, wherein said matrix member has a loop opening formed by bonding both longitudinal side ends of a ring of fabric to said matrix member, wherein the method further comprises providing a string, and wherein fixing said matrix member over said microphone head comprises passing said string through said loop opening.

6. A deodorant cover for a microphone, comprising:

a matrix member comprising paper having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone.

7. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a band, a part of said band being fixed to said matrix member, and wherein at least one end of said band is provided with adhesive.

8. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a loop opening formed along a peripheral part of said matrix member, and a string positioned in said loop opening.

9. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises stretchable pleats formed on a peripheral part of said matrix member.

10. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a loop opening formed on a peripheral part of said matrix member formed to have said configuration, and a ring member capable of being positioned in said loop opening.

11. The deodorant cover of claim 10, wherein said matrix member is formed to have said configuration by die-forging said matrix member using shaping dies.

12. The deodorant cover of claim 10, wherein said ring member is a double-winding ring, a part of said double-winding ring capable of being positioned outside of said loop opening.

13. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a retainer having an inserting hole into which a grip of said microphone is capable of being fitted, and a fixing portion which is capable of being fixed to said retainer, said fixing portion being integrally formed on a peripheral portion of said matrix member, wherein said fixing element further comprises adhesive provided on that surface of said fixing portion which faces said retainer, so that said fixing portion is fixed to said retainer using said adhesive.

14. The deodorant cover of claim 13, wherein said matrix member is formed to have said configuration by die-forging said matrix member using shaping dies.

15. The deodorant cover of claim 13, wherein said retainer has a radial length capable of keeping said microphone head off a horizontal surface when said microphone is placed on said horizontal surface.

16. The deodorant cover of claim 13, wherein said retainer comprises rubber.

17. The deodorant cover of claim 13, wherein said retainer comprises polyurethane foam.

18. The deodorant cover of claim 13, wherein said retainer comprises an elastic synthetic resin.

19. The deodorant cover of claim 13, wherein said retainer comprises paperboard.

20. The deodorant cover of claim 13, wherein said retainer comprises wood.

21. The deodorant cover of claim 13, wherein said retainer comprises a cushioning medium at least along a peripheral edge of said retainer.

22. The deodorant cover of claim 13, wherein said matrix member bears a pattern printed thereon.

23. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a retainer having an inserting hole into which a grip of said microphone is capable of being fitted, and a fixing portion which is capable of being fixed to said retainer, said fixing portion being integrally formed on a peripheral portion of said matrix member, wherein said fixing element further comprises double-sided adhesive tape, one side of said double-sided adhesive tape being fixed to that surface of said fixing portion which faces said retainer, and wherein an other side of said double-sided adhesive tape is capable of being exposed to adhere to said retainer when said matrix member is fixed to said microphone head.

24. A deodorant cover for a microphone, comprising:

a matrix member having a predetermined configuration which corresponds to a head of a microphone, wherein said matrix member carries a calcium phosphate compound having a Ca/P ratio in a range of about 1.0 to 2.0; and a fixing element for fixing said matrix member to the head of the microphone, wherein said fixing element comprises a retainer having an inserting hole into which a grip of said microphone is capable of being fitted, and a fixing portion which is capable of being fixed to said retainer, said fixing portion being integrally formed on a peripheral portion of said matrix member, wherein said fixing element further comprises a hook tape and a loop tape, and wherein one of said hook tape and said loop tape is fixed to that surface of said fixing position which faces said retainer and the other of said hook tape and said loop tape is fixed to that surface of said retainer which faces said fixing portion, so that said fixing portion is fixed to said retainer through said hook tape and said loop tape.

25. A deodorant cover for a microphone, comprising:
a matrix member having a predetermined configuration which corresponds to a head of a microphone, wherein said matrix member carries a calcium phosphate compound having a Ca/P ratio in a range of about 1.0 to 2.0; and
a fixing element for fixing said matrix member to the head of the microphone, wherein said fixing element comprises a retainer having an inserting hole into which a grip of said microphone is capable of being fitted, and a fixing portion which is capable of being fixed to said retainer, said fixing portion being integrally formed on a peripheral portion of said matrix member, wherein said fixing element further comprises an annular fixing member which is capable of fitting on said retainer with said fixing portion held between said annular fixing member and said retainer.

26. The deodorant cover of claim 25, wherein said annular fixing member comprises a cushioning medium at least along a peripheral edge of said fixing member.

27. The deodorant cover of claim 26, wherein said cushioning medium comprises rubber.

28. The deodorant cover of claim 26, wherein said cushioning medium comprises polyurethane foam.

29. The deodorant cover of claim 26, wherein said cushioning medium comprises an elastic material of a synthetic resin.

30. A deodorant cover for a microphone, comprising:
a matrix member having a predetermined configuration which corresponds to a head of a microphone, wherein said matrix member carries a calcium phosphate compound having a Ca/P ratio in a range of about 1.0 to 2.0; and
a fixing element for fixing said matrix member to the head of the microphone, wherein said fixing element comprises a first annular member capable of being detachably fixed to an approximate top end of a grip of said microphone with said first annular member capable of surrounding said approximate top end, and a second annular member capable of being detachably fitted on said first annular member, and wherein a peripheral part of said matrix member is capable of being held between said first annular member and said second annular member.

31. The deodorant cover of claim 30, wherein said first annular member comprises an inner cylindrical portion which is capable of surrounding said approximate top end of said grip,
and wherein said second annular member comprises an outer cylindrical portion capable of being fitted on said inner cylindrical portion of said first annular member,
and further wherein said peripheral part of said matrix member is capable of being held between said inner cylindrical portion and said outer cylindrical portion.

32. The deodorant cover according to claim 31, wherein said outer cylindrical portion is capable of being fitted on said inner cylindrical portion with a gap formed therebetween, said peripheral part of said matrix member being capable of being positioned in said gap.

33. The deodorant cover of claim 31, wherein a plurality of projections are formed on at least one of an outer peripheral surface of said inner cylindrical portion and an inner peripheral surface of said outer cylindrical portion.

34. The deodorant cover of claim 33, wherein said plurality of projections are formed at substantially regular intervals.

35. The deodorant cover of claim 33, wherein each of said plurality of projections extends substantially in parallel to an axial direction of said annular member having said projections.

36. The deodorant cover of claim 31, wherein an outer peripheral surface of said inner cylindrical portion tapers toward a top of said head when said inner cylindrical portion surrounds said grip, and wherein an inner peripheral surface of said outer cylindrical portion, which is capable of facing said tapering outer peripheral surface, tapers toward said top of said head substantially in parallel to said tapering outer peripheral surface when said outer cylindrical portion is fitted on said inner cylindrical portion.

37. The deodorant cover of claim 36, wherein a plurality of projections are formed on at least one of said outer peripheral surface of said inner cylindrical portion and said inner peripheral surface of said outer cylindrical portion.

38. The deodorant cover of claim 37, wherein said plurality of projections are formed at substantially regular intervals.

39. The deodorant cover of claim 37, wherein each of said plurality of projections extends substantially in parallel to an axial direction of said annular member having said projections.

40. The deodorant cover of claim 30, wherein said first annular member comprises a pair of semi-cylindrical pieces openably connected to each other.

41. The deodorant cover of claim 40, wherein said first annular member further comprises an element for locking said pair of semi-cylindrical pieces so as to restrict said pair of semi-cylindrical pieces from being opened.

42. The deodorant cover of claim 40, wherein said first annular member further comprises a thin flexible portion which connects said pair of semi-cylindrical pieces.

43. The deodorant cover of claim 42, wherein said first annular member comprises plastic, said thin flexible portion and said pair of semi-cylindrical pieces being integrally formed.

44. The deodorant cover of claim 30, wherein said second annular member has a radial length capable of keeping said microphone head off a horizontal surface when said microphone is placed on said horizontal surface.

45. The deodorant cover of claim 44, wherein said second annular member comprises a cushioning medium at least along a peripheral edge of said second annular member.

46. A method for associating a matrix member to a microphone head, comprising:
providing a microphone comprising a microphone head;
providing a matrix member having a configuration corresponding to said microphone head, wherein said matrix member carries a calcium phosphate compound having a Ca/P ratio in a range of about 1.0 to 2.0, wherein said matrix member comprises stretchable pleats formed on a peripheral part of said matrix member; and
fixing said matrix member over said microphone head, wherein fixing said matrix member over said microphone head comprises stretching said stretchable pleats over said microphone head.

47. A method for associating a matrix member to a microphone head, comprising:

providing a microphone comprising a microphone head and a grip;

providing a matrix member having a configuration corresponding to said microphone head, wherein said matrix member carries a calcium phosphate compound having a Ca/P ratio in a range of about 1.0 to 2.0;

providing a fixing portion integrally formed on a peripheral portion of said matrix member;

providing a retainer having a hole;

providing a hook tape and a loop tape, wherein one of said hook tape and said loop tape is fixed to a surface of said fixing portion and the other of said hook tape and said loop tape is fixed to a surface of said retainer; and fixing said matrix member over said microphone head, wherein fixing said matrix member over said microphone head comprises inserting said grip of said microphone into said hole of said retainer and fixing said fixing portion to said retainer through said hook tape and said loop tape.

48. A method for associating a matrix member to a microphone head, comprising:

providing a microphone comprising a microphone head;

providing a matrix member having a configuration corresponding to said microphone head, wherein said matrix member carries a calcium phosphate compound having a Ca/P ratio in a range of about 1.0 to 2.0, wherein said matrix member comprises a loop opening formed on a peripheral part of said matrix member;

providing a double-winding ring; and fixing said matrix member over said microphone head, wherein fixing said matrix member over said microphone head comprises inserting at least a part of said double-winding ring inside said loop opening.

49. A method for associating a matrix member to a microphone head, comprising:

providing a microphone comprising a microphone head and a grip;

providing a matrix member having a configuration corresponding to said microphone head, wherein said matrix member carries a calcium phosphate compound having a Ca/P ratio in a range of about 1.0 to 2.0;

providing a fixing portion integrally formed on a peripheral part of said matrix member;

providing a retainer having a hole;

providing an annular fixing member for fitting on said retainer; and fixing said matrix member over said microphone head, wherein fixing said matrix member over said microphone head comprises inserting said grip of said microphone into said hole of said retainer and fitting said annular fixing member on said retainer to hold said fixing portion between said annular fixing member and said retainer.

50. A method for associating a matrix member to a microphone head, comprising:

providing a microphone comprising a microphone head and a grip;

providing a matrix member having a configuration corresponding to said microphone head, wherein said matrix member carries a calcium phosphate compound having a Ca/P ratio in a range of about 1.0 to 2.0;

providing a fixing portion integrally formed on a peripheral portion of said matrix member;

providing a retainer having a hole;

providing a double-sided adhesive tape, wherein one side of said double-sided adhesive tape is for fixing to said fixing portion and the other side of said double-sided adhesive tape is for fixing to said retainer; and fixing said matrix member over said microphone head, wherein fixing said matrix member over said microphone head comprises inserting said grip of said microphone into said hole of said retainer and fixing said fixing portion to said retainer through said double-sided adhesive tape.

51. A method for associating a matrix member to a microphone head, comprising:

providing a microphone comprising a microphone head and a grip;

providing a matrix member having a configuration corresponding to said microphone head, wherein said matrix member carries a calcium phosphate compound having a Ca/P ratio in a range of about 1.0 to 2.0, wherein said matrix member comprises a peripheral part;

providing a first annular member for detachably fixing and surrounding an approximate top end of said grip of said microphone;

providing a second annular member for detachably fitting on said first annular member; and fixing said matrix member over said microphone head, wherein fixing said matrix member over said microphone head comprises fixing said first annular member on an approximate top end of said grip of said microphone and holding said peripheral part of said matrix member between said first annular member and said second annular member by fitting said second annular member on said first annular member.

* * * * *